United States Patent [19]

Larson, Jr. et al.

[11] Patent Number: 5,693,091
[45] Date of Patent: Dec. 2, 1997

[54] ARTIFICIAL HEART AND METHOD OF MAINTAINING BLOOD FLOW

[75] Inventors: Carl O. Larson, Jr., Stonington; James S. Smith, Old Lyme; John H. Chapman, Groton; Scot A. Slimon, Mystic; John D. Trahan, N. Stonington, all of Conn.; Robert J. Brozek, Bridgewater, N.J.; Alberto Franco, Hazlet, N.J.; John J. McGarvey; Marvin E. Rosen, both of Elizabeth, N.J.; Michael K. Pasque, St. Louis, Mo.

[73] Assignee: Electric Boat Corporation, Groton, Conn.

[21] Appl. No.: 480,824

[22] Filed: Jun. 7, 1995

Related U.S. Application Data

[60] Division of Ser. No. 201,806, Feb. 25, 1994, Pat. No. 5,676,651, and a continuation-in-part of Ser. No. 35,788, Mar. 23, 1993, Pat. No. 5,290,227, which is a continuation-in-part of Ser. No. 926,779, Aug. 6, 1992, abandoned.

[51] Int. Cl.⁶ ................................................... A61M 1/10
[52] U.S. Cl. .................................................... 612/3
[58] Field of Search .................................... 623/3

[56] References Cited

U.S. PATENT DOCUMENTS

| | | |
|---|---|---|
| 424,535 | 4/1890 | Bock . |
| 458,872 | 9/1891 | Van Depoele . |
| 1,684,468 | 9/1928 | Brown . |
| 1,822,242 | 9/1931 | Schongut . |
| 2,061,869 | 11/1936 | Gilbert et al. . |
| 2,515,110 | 7/1950 | Bornstein . |
| 2,690,128 | 9/1954 | Basilewsky . |
| 2,701,331 | 2/1955 | Holst . |
| 3,134,938 | 5/1964 | Morgan . |
| 3,172,027 | 3/1965 | Bourke et al. . |
| 3,233,607 | 2/1966 | Bolie . |
| 3,282,219 | 11/1966 | Blackwell et al. . |
| 3,287,616 | 11/1966 | McNeile . |
| 3,328,656 | 6/1967 | Dotson . |
| 3,443,128 | 5/1969 | Fakan . |
| 3,492,819 | 2/1970 | Waltrip . |
| 3,791,770 | 2/1974 | Farkos . |
| 3,836,289 | 9/1974 | Wolford et al. . |

(List continued on next page.)

FOREIGN PATENT DOCUMENTS

| | | |
|---|---|---|
| 0350302 | 11/1975 | European Pat. Off. . |
| 0203222 | 11/1985 | European Pat. Off. . |
| 0198617 | 3/1986 | European Pat. Off. . |
| 0237145 | 1/1987 | European Pat. Off. . |
| 0310254 | 9/1988 | European Pat. Off. . |
| 2309206 | 11/1976 | France . |
| 2812481 | 3/1978 | Germany . |
| WO93-09348 | 5/1993 | WIPO . |

OTHER PUBLICATIONS

English language abstract of FR 2 309 206.
English language abstract of Soviet Union Patent No. 1,284,556, Jan. 23, 1987.

(List continued on next page.)

*Primary Examiner*—William E. Kamim
*Attorney, Agent, or Firm*—Brumbaugh, Graves, Donohue & Raymond

[57] ABSTRACT

In one embodiment described in the specification, a surgically implantable reciprocating pump employs a check valve as the piston, which is driven by a permanent magnet linear electric motor to assist either side of the natural heart. The pump is implanted in the aorta or pulmonary artery using vascular attachment cuffs such as flexible cuffs for suturing at each end with the pump output directly in line with the artery. The pump is powered by surgically implanted rechargeable batteries. In another embodiment, pairs of pumps are provided to replace or assist the natural heart or to provide temporary blood flow throughout the body, for example, during operations to correct problems with the natural heart.

15 Claims, 22 Drawing Sheets

U.S. PATENT DOCUMENTS

| | | |
|---|---|---|
| 3,842,440 | 10/1974 | Karlson . |
| 3,884,125 | 5/1975 | Massie . |
| 3,911,897 | 10/1975 | Leachman, Jr. . |
| 3,911,898 | 10/1975 | Leachman, Jr. . |
| 3,919,722 | 11/1975 | Harmison . |
| 4,005,346 | 1/1977 | Hsia . |
| 4,016,871 | 4/1977 | Schiff . |
| 4,101,816 | 7/1978 | Shepter . |
| 4,102,610 | 7/1978 | Taboada et al. . |
| 4,127,134 | 11/1978 | Ushakoff . |
| 4,210,409 | 7/1980 | Child . |
| 4,213,207 | 7/1980 | Wilson . |
| 4,220,899 | 9/1980 | von der Heide . |
| 4,221,548 | 9/1980 | Child . |
| 4,233,690 | 11/1980 | Akins . |
| 4,234,831 | 11/1980 | Kemmer et al. . |
| 4,262,414 | 4/1981 | Sugalski . |
| 4,272,226 | 6/1981 | Osborne . |
| 4,299,544 | 11/1981 | Masaka . |
| 4,332,541 | 6/1982 | Anders . |
| 4,344,022 | 8/1982 | von der Heide . |
| 4,370,577 | 1/1983 | Wakabayashi et al. . |
| 4,375,941 | 3/1983 | Child . |
| 4,389,169 | 6/1983 | De Dionigi . |
| 4,397,049 | 8/1983 | Robinson et al. . |
| 4,397,919 | 8/1983 | Ballard . |
| 4,434,389 | 2/1984 | Kollmorgen et al. . |
| 4,500,827 | 2/1985 | Merritt et al. . |
| 4,506,394 | 3/1985 | Bédard . |
| 4,516,567 | 5/1985 | Veragen . |
| 4,535,483 | 8/1985 | Klawitter et al. . |
| 4,541,787 | 9/1985 | DeLong . |
| 4,583,525 | 4/1986 | Suzuki et al. . |
| 4,610,658 | 9/1986 | Buchwald et al. . |
| 4,638,192 | 1/1987 | von der Heide . |
| 4,642,882 | 2/1987 | Castiglione et al. . |
| 4,650,486 | 3/1987 | Chareire . |
| 4,687,623 | 8/1987 | Cook . |
| 4,692,673 | 9/1987 | DeLong . |
| 4,705,516 | 11/1987 | Barone et al. . |
| 4,775,301 | 10/1988 | Cartwright et al. . |
| 4,790,843 | 12/1988 | Carpenter et al. . |
| 4,824,337 | 4/1989 | Lindner et al. . |
| 4,846,831 | 7/1989 | Skillin . |
| 4,868,431 | 9/1989 | Karita et al. . |
| 4,870,306 | 9/1989 | Petersen . |
| 4,892,541 | 1/1990 | Alonso . |
| 4,896,088 | 1/1990 | Jahns . |
| 4,897,563 | 1/1990 | Bahl . |
| 4,924,123 | 5/1990 | Hamajima et al. . |
| 4,935,030 | 6/1990 | Alonso . |
| 4,957,504 | 9/1990 | Chardack . |
| 4,965,864 | 10/1990 | Roth et al. . |
| 4,973,892 | 11/1990 | Murata et al. . |
| 4,979,955 | 12/1990 | Smith . |
| 5,035,709 | 7/1991 | Wieting et al. . |
| 5,064,353 | 11/1991 | Tsukahara . |
| 5,071,431 | 12/1991 | Sauter et al. . |
| 5,081,381 | 1/1992 | Narasaki . |
| 5,085,563 | 2/1992 | Collins et al. . |
| 5,089,014 | 2/1992 | Holfert . |
| 5,089,017 | 2/1992 | Young et al. . |
| 5,091,665 | 2/1992 | Kelly . |
| 5,123,919 | 6/1992 | Sauter et al. . |
| 5,136,194 | 8/1992 | Oudet et al. . |
| 5,146,123 | 9/1992 | Yarr . |
| 5,163,954 | 11/1992 | Curcio et al. . |
| 5,166,563 | 11/1992 | Bassine . |
| 5,178,633 | 1/1993 | Peters . |
| 5,179,306 | 1/1993 | Nasar . |
| 5,193,985 | 3/1993 | Escue et al. . |
| 5,207,707 | 5/1993 | Gourley . |
| 5,208,498 | 5/1993 | Hamajima . |
| 5,214,323 | 5/1993 | Ueda et al. . |
| 5,225,725 | 7/1993 | Shiraki et al. . |
| 5,236,451 | 8/1993 | Bokros et al. . |
| 5,242,995 | 9/1993 | Kim et al. . |
| 5,246,453 | 9/1993 | Bokros et al. . |
| 5,252,043 | 10/1993 | Bolding et al. . |
| 5,263,979 | 11/1993 | Isoyama et al. . |
| 5,360,445 | 11/1994 | Goldowsky . |

OTHER PUBLICATIONS

Article entitled: Engineering A Replacement For The Human Heart, Mechanical Engineering, Jul. 1991, pp. 36–43.

Daniel, Michael A., et al., "Clinical Evaluation of the Novacor Totally Implantable Ventricular Assist System", ASAIO Transactions 1991; 37:M423–M425.

Dörp, E., et al., "The measurement of blood density to investigate protein deposition at the blood/hollow fiber membrane interface during ultrafiltration", Int J Artif Organs 1991; 14:424–429.

Drasler, William J., et al., "A Unique Vascular Graft Concept for Coronary and Peripheral Applications", ASAIO Transactions 1988; 34: 769–772.

Fischel, R.J., et al., "Couette Membrane Filtration with Constant Shear Stress", ASAIO Transactions 1988; 34:375–385.

Frazier, O.H., M.D., et al., "First Human Use of the Hemopump, a Catheter–Mounted Ventricular Assist Device", Ann Thorac Surg 1990; 49:299–304.

Haas, G., et al., "Effect of head–down bedrest on blood/plasma density after intravenous fluid load", Acta Physiol Scand 1992, 144, S604:113–120.

Hung, Ting–Cheng, et al., "Effects of Long–term Novacor Artificial Heart Support on Blood Rheology", ASAIO Transactions 1991; 37:M312–M313.

Hashimoto, Shigehiro, "Erythrocyte Destruction under Periodically Fluctuating Shear Rate: Comparative Study with Constant Shear Rate", Artif Organs 1989; 13(5):458–463.

Imachi, Kou, et al., "A New Pulsatile Total Artificial Heart Using a Single Centrifugal Pump", ASAIO Transactions 1991; 37:M242–M243.

Jurmann, Michael J., et al., "In Vivo Determinants of Energy Consumption in Electric Motor Driven Artificial Hearts", ASAIO Transactions 1989; 35:745–747.

Kenner, L, "The measurement of blood density and its meaning", Basic Res Cardiol 1989; 84:111–124.

Kim, Hee Chan, et al., "Development of An Automatic Control Algorithm for the Electrohydraulic Total Artificial Heart Without Transducers", ASAIO Transactions 1991; 37:M501–M503.

Kresh, J. Yasha, "Myocardial Mechanics and Energetics Revisited", Trans Am Soc Artif Intern Organs 1991; 37:537–539.

Lamson, Theodore C., et al., "Real–Time In Vitro Observation of Cavitation in a Prosthetic Heart Valve", ASAIO Transactions 1991; 37:M351–M353.

Lee, Jen–shih and Lee, Lian–pin, "A Density Method for Determining Plasma and Red Blood Cell Volume", Annals of Biomedical Engineering 1992; 20:195–204.

Lee, Sang H., et al., "Development of A Totally Implantable Total Artificial Heart Controller", ASAIO Transactions 1991; 37:M505–M507.

Levinson, Mark M., M.D., et al., "Indexes of Hemolysis in Human Recipients of the Jarvik–7 Total Artificial Heart: A Cooperative Report of Fifteen Patients", J. Heart Transplant 1986; 5:236–248.

Lioi, Anthony P., "In Vitro Development of Automatic Control for the Actively Filled Electrohydraulic Heart", Artif Organs 1988; 12(2) 152–162.

McGee, Michael G. et al., "Extended Support with a Left Ventricular Assist Device as a Bridge to Heart Transplantation", ASAIO Transactions 1991; 37:M425–M426.

Miller, Douglas L., et al., "Mechanisms For Hemolysis By Ultrasonic Cavitation In The Rotating Exposure System", Ultrsound in Med & Biol 1991; 17(2):171–178.

Mitamura, Yoshinori, et al., "The Valvo–Pump: An Axial, Nonpulsatile Blood Pump", ASAIO Transactions 1991; 37:M510–M512.

Nakahara, Toro and Yoshida, Fumitake, "Mechanical effects on rates of hemolysis", Journal of Biomedical Materials Research 1986; 20:363–374.

Oaks, Timothy E., "Combined Registry for the Clinical Use of Mechanical Ventricular Assist Pumps and the Total Artificial Heart in Conjunction with Heart Transplantation: Fifth Official Report–1990", The Journal of Heart & Lung Transplantation 1991, vol. 10, No. 5, Part 1, pp. 621–625.

Perrone, B., "Evidence of Fluid Shifts during Dialysis Sessions with Sodium and Ultrafiltration Profiles", Contrib Nephrol. Basel, Karger 1989; 74: 191–199.

Pierce, William S., M.D., et al., "An Electric Artificial Heart for Clinical Use", Ann Surg 1990, pp. 339–344.

Poirier, Victor L., "Can Our Society Afford Mechanical Hearts?", ASAIO Transactions 1991; 37:540–544.

Qian, Kun–xi, "Experience in Reducing the Hemolysis of an Impeller Assist Heart", ASAIO Transactions 1989; 35:46–53.

Qian, Kun–xi, "Haemodynamic approach to reducing thrombosis and haemolysis in an impeller pump", Biomechs 1990; 12:533–535.

Qian, K.X., et al., "The Realization of a Pulsatile Implantable Impeller Pump with Low Hemolysis", ASAIO Transactions 1989; 13:162–169.

Qian, K.X., et al., "Toward an Implantable Impeller Total Heart", ASAIO Transactions 1987; 33:704–707.

Sasaki, Tatsuya, et al., "A Biolized, Compact, Low Noise, High Performance Implantable Electromechanical Ventricular Assist System", ASAIO Transactions 1991; 37:M249–251.

Schneditz, D., et al., "Methods in clinical hemorheology: The continuous measurement of arterial blood density and blood sound speed in man", Biorheology 1990; 27:895–902.

Schneditz, D., "Sound Speed, Density and Total Protein Concentration of Blood", J. Clin. Chem. Clin. Biochem. 1989; 27:803–806.

Schoen, Frederick J., "Biomaterials Science, Medical Devices, and Artificial Organs", ASAIO Transactions 1991; 37:44–48.

Schoephoerster, Richard T. and Chandran, Krishnan B., "Velocity and Turbulence Measurements Past Mitral Valve Prostheses In A Model Left Ventricle", J. Biomechanics 1991; 24(7):549–562.

Shah, Aamir S., et al., "Intraoperative Determination of Mediastinal Constraints for a Total Artificial Heart", Trans Am Soc Artif Intern Organs 1991, vol. XXXVII, pp. 76–79.

Shiono, Motomi, et al., "Antomic Fit Study for Development of a One Piece Total Artificial Heart", ASAIO Transactions 1991; 37:M254–M255.

Snyder, A., et al., "A Completely Implantable Total Artificial Heart System", ASAIO Transactions 1991; 37:M237–M238.

Taenaka, Yoshiyuki, et al., "Chronic Evaluation of a Compact Nonseal Magnet Pump as a Nonpulsatile Pump for Long–term Use", ASAIO Transactions 1991; 37:M243–M245.

Takatani, S., et al., "A Unique, Efficient, Implantable, Electromechanical, Total Artificial Heart", ASAIO Transactions 1991; 37:M238–M240.

Trinkl, J., et al., "Control of Pulsatile Rotary Pumps Without Pressure Sensors", ASAIO Transactions 1991; 37:M208–M210.

Tsach, Uri, et al., "Minimum Power Consumption of the Electric Ventricular Assist Device Through the Design of an Optimal Output Controller", ASAIO Transactions 1987; 38:714–719.

Van Meurs, Krisa P., et al., "Maximum Blood Flow Rates for Arterial Cannulae Used in Neonatal ECMO", ASAIO Transactions 1990; 36:M679–M681.

Wampler, Richard K., et al., "In Vivo Evaluation of a Peripheral Vascular Access Axial Flow Blood Pump", Trans Am Soc Artif Intern Organs 1988, vol. XXXIV, pp. 450–454.

Weiss, William J., et al., "In Vivo Performance of a Transcutaneous Energy Transmission System with the Penn State Motor Driven Ventricular Assist Device", ASAIO Transactions 1989; 35:284–288.

Weiss, William J., et al., "Permanent Circulatory Support Systems at The Pennsylvania State University", IEE Transactions on Biomedical Engineering 1990, vol. 37, No. 2, pp. 138–145.

Wipf, Stefan L., "Spherical Rotary Piston Machine as an Artificial Heart", ASAIO Transactions 1991; 37:M246–M247.

Woodard, John C., et al., "A Sophisticated Electromechanical Ventricular Simulator for Ventricular Assist System Testing", ASAIO Transactions 1991; 37:M210–M211.

Yoganathan, Ajit P., Ph.D., et al., "In vitro velocity and turbulence measurements in the vicinity of three new mechanical aortic heart valve prostheses: Björk–Shiley Monostrut, Omni–Carbon, and Duromedics", J. Thoracic Cardiovasc Surg 1988; 95:929–939.

Cathey, Jimmie J. et al., "A Tubular Self–Synchronous Motor for Artificial Heart Pump Drive", IEEE Transactions on Biomedical Engineering, Mar. 1996, vol. BME–33, No. 3, pp. 315–319.

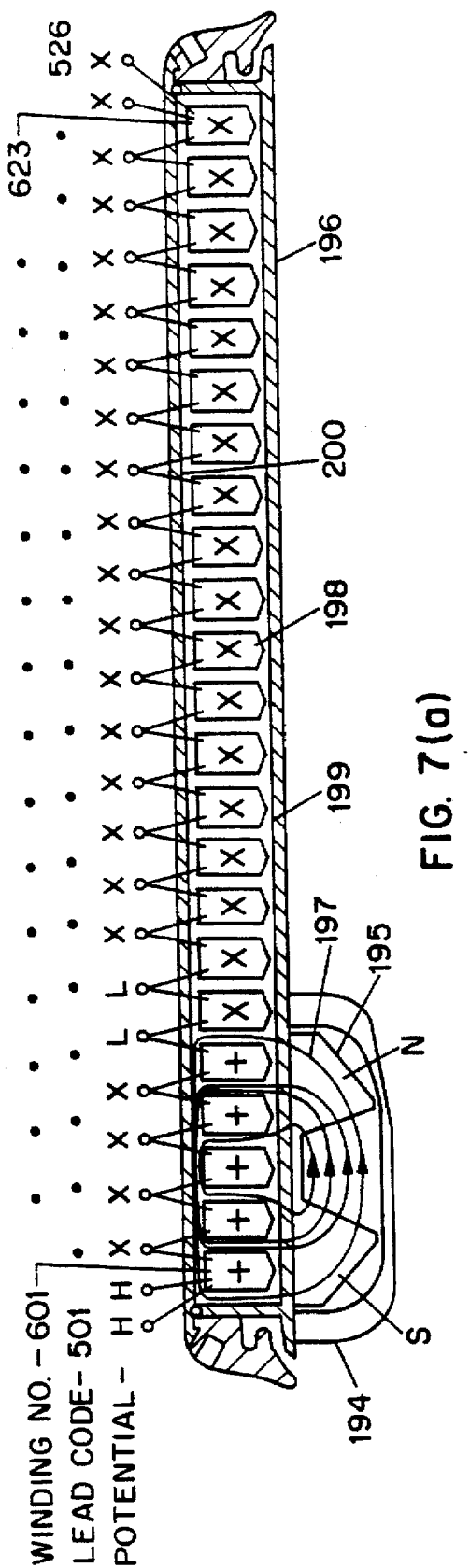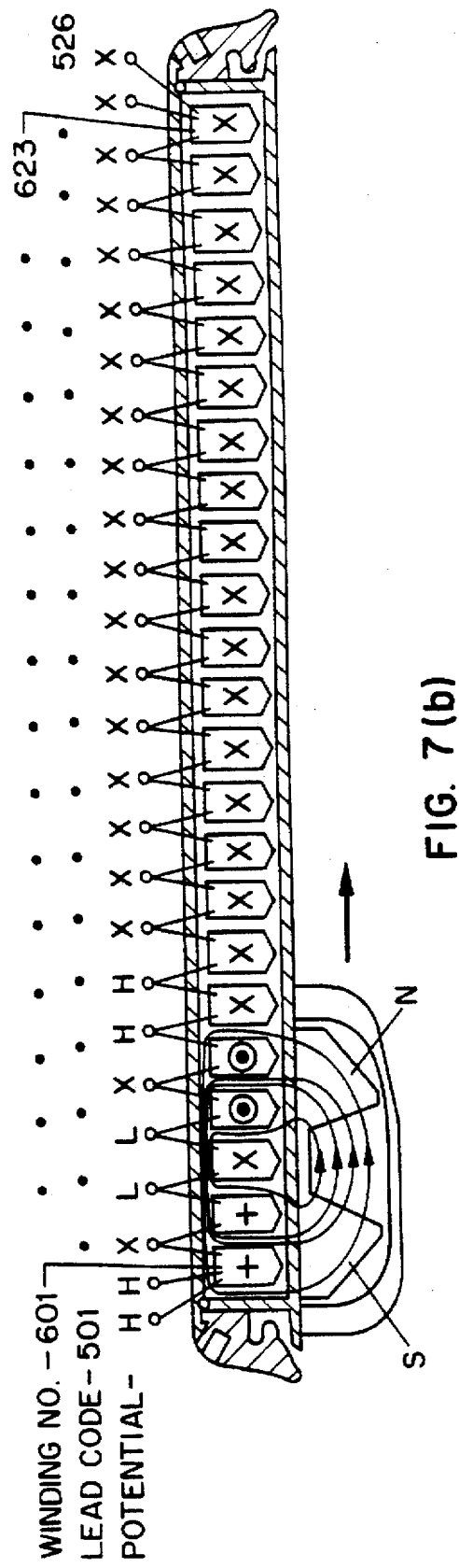

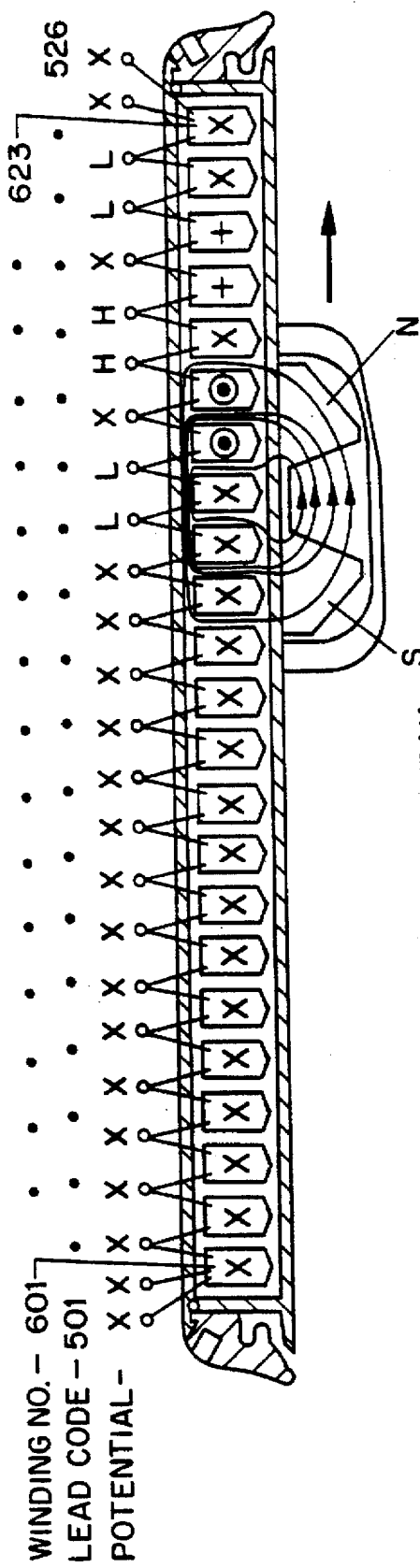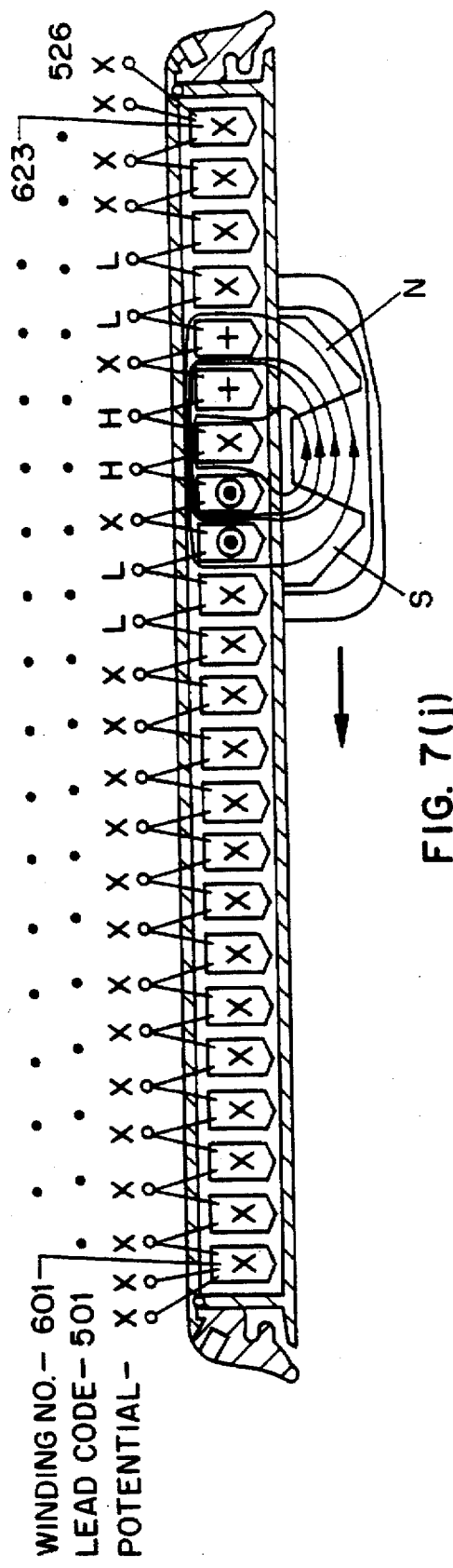

ARTIFICIAL HEART AND METHOD OF MAINTAINING BLOOD FLOW

CROSS-REFERENCE TO RELATED APPLICATIONS

This application is a division of U.S. Ser. No. 08/201,806 filed on Feb. 25, 1994, now U.S. Pat. No. 5,676,651 which is a continuation-in-part of U.S. Ser. No. 08/035,788 filed Mar. 23, 1993, now U.S. Pat. No. 5,290,227 which is a continuation-in-part of U.S. Ser. No. 07/926,779 filed Aug. 6, 1992 now abandoned.

BACKGROUND OF THE INVENTION

This invention relates to reciprocating pump arrangements for pumping fluids such as blood in a controlled manner. More specifically, this invention is directed to a reciprocating pump capable of providing optimal assistance for ventricular or cardiac support such as that for an ailing ventricle. It produces effective pumping action under minimum shear conditions.

Heretofore a number of pump designs have been proposed for pumping fluids such as blood. Such pumps must provide leak-free operation and must avoid contamination of the fluid by the pump components and the external environment. In addition, such pumps must effectively pump the fluid at a suitable rate without applying excessive Reynolds shear stress to the fluid. Damage due to excessive shear is particularly a problem when pumping fluids such as blood or blood products.

It is well known to those skilled in the art that lysis or cell destruction may result from application of shear stress to cell membranes. Red blood cells are particularly susceptible to shear stress damage as their cell membranes do not include a reinforcing cytoskeleton to maintain cell shape. Lysis of white blood cells and platelets also occurs upon application of high shear stress. Lysis of red blood cells can result in release of cell contents which trigger subsequent platelet aggregation. Sublytic shear stress leads to cellular alterations and direct activation and aggregation of platelets and white blood cells.

Several types of surgically implantable pumps have been developed in an effort to provide a mechanical device for augmenting or replacing the blood pumping action of damaged or diseased hearts. Some of these pumps are designed to support single ventricular function. Such pumps usually support the left ventricle, which pumps blood to the entire body except the lungs, since it becomes diseased far more commonly than the right ventricle, which pumps blood only to the lungs. Other devices have been tested and used for providing biventricular function.

Depending on the needs of a particular patient and the design of a pump, pumping units such as so-called "VADs" (ventricular assist devices) can be implanted to assist a functioning heart that does not have adequate pumping capability. Other types of pumps, such as the so-called "Jarvik heart," can be used to completely replace a heart which has been surgically removed.

Temporary as well as permanent implantable pumps have been developed. "Permanent" in this sense refers to the remaining life of the patient; after a patient's death, any artificial pumping device is usually removed for analysis. "Temporary" implantation usually involves (1) an attempt to reduce the stress on a heart while it recovers from surgery or some other short-term problem, or (2) use of a pump as a "bridge" to forestall the death of a patient until a suitable donor heart can be found for cardiac transplantation.

The most widely tested and commonly used implantable blood pumps employ variable forms of flexible sacks (also spelled sacs) or diaphragms which are squeezed and released in a cyclical manner to cause pulsatile ejection of blood. Such pumps are discussed in books or articles such as Hogness and Antwerp 1991, DeVries et al 1984, and Farrar et al 1988, and in U.S. pat. No. 4,994,078 (Jarvik 1991), 4,704,120 (Slonina 1987), 4,936,758 (Coble 1990), and 4,969,864 (Schwarzmann et al 1990). Sack or diaphragm pumps are subject to fatigue failure of compliant elements and as such are mechanically and functionally quite different from the pump which is the subject of the present invention.

An entirely different class of implantable blood pumps uses rotary pumping mechanisms. Most rotary pumps can be classified into two categories: centrifugal pumps and axial pumps. Centrifugal pumps, which include pumps marketed by Sarns (a subsidiary of the 3M Company) and Biomedicus (a subsidiary of Medtronic, Eden Prairie, MN), direct blood into a chamber, against a spinning interior wall (which is a smooth disk in the Medtronic pump). A flow channel is provided so that the centrifugal force exerted on the blood generates flow.

By contrast, axial pumps provide blood flow along a cylindrical axis, which is in a straight (or nearly straight) line with the direction of the inflow and outflow. Depending on the pumping mechanism used inside an axial pump, this can in some cases reduce the shearing effects of the rapid acceleration and deceleration forces generated in centrifugal pumps. However, the mechanisms used by axial pumps can inflict other types of stress and damage on blood cells.

Some types of axial rotary pumps use impeller blades mounted on a center axle, which is mounted inside a tubular conduit. As the blade assembly spins, it functions like a fan, or an outboard motor propeller. As used herein, "impeller" refers to angled vanes (also called blades) which are constrained inside a flow conduit; an impeller imparts force to a fluid that flows through the conduit which encloses the impeller. By contrast, "propeller" usually refers to non-enclosed devices, which typically are used to propel vehicles such as boats or airplanes.

Another type of axial blood pump, called the "Haemopump" (sold by Nimbus) uses a screw-type impeller with a classic screw (also called an Archimedes screw; also called a helifoil, due to its helical shape and thin cross-section). Instead of using several relatively small vanes, the Haemopump screw-type impeller contains a single elongated helix, comparable to an auger used for drilling or digging holes. In screw-type axial pumps, the screw spins at very high speed (up to about 10,000 rpm). The entire Haemopump unit is usually less than a centimeter in diameter. The pump can be passed through a peripheral artery into the aorta, through the aortic valve, and into the left ventricle. It is powered by an external motor and drive unit.

Centrifugal or axial pumps are commonly used in three situations: (1) for brief support during cardio-pulmonary operations, (2) for short-term support while awaiting recovery of the heart from surgery, or (3) as a bridge to keep a patient alive while awaiting heart transplantation. However, rotary pumps generally are not well tolerated for any prolonged period. Patients who must rely on these units for a substantial length of time often suffer from strokes, renal (kidney) failure, and other organ dysfunction. This is due to the fact that rotary devices, which must operate at relatively high speeds, may impose unacceptably high levels of turbulent and laminar shear forces on blood cells. These forces can damage or lyse (break apart) red blood cells. A low blood count (anemia) may result, and the disgorged contents of lysed blood cells (which include large quantities of hemoglobin) can cause renal failure and lead to platelet activation that can cause embolisms and stroke.

One of the most important problems in axial rotary pumps in the prior art involves the gaps that exist between the outer edges of the blades, and the walls of the flow conduit. These gaps are the site of severe turbulence and shear stresses, due to two factors. Since implantable axial pumps operate at very high speed, the outer edges of the blades move extremely fast and generate high levels of shear and turbulence. In addition, the gap between the blades and the wall is usually kept as small as possible to increase pumping efficiency and to reduce the number of cells that become entrained in the gap area. This can lead to high-speed compression of blood cells as they are caught in a narrow gap between the stationary interior wall of the conduit and the rapidly moving tips or edges of the blades.

An important factor that needs to be considered in the design and use of implantable blood pumps is "residual cardiac function," which is present in the overwhelming majority of patients who would be candidates for mechanical circulatory assistance. The patient's heart is still present and still beating, even though, in patients who need mechanical pumping assistance, its output is not adequate for the patient's needs. In many patients, residual cardiac functioning often approaches the level of adequacy required to support the body, as evidenced by the fact that the patient is still alive when implantation of an artificial pump must be considered and decided. If cardiac function drops to a level of severe inadequacy, death quickly becomes imminent, and the need for immediate intervention to avert death becomes acute.

Most conventional ventricular assist devices are designed to assume complete circulatory responsibilities for the ventricle they are "assisting." As such, there is no need, nor presumably any advantage, for the device to interact in harmony with the assisted ventricle. Typically, these devices utilize a "fill-to-empty" mode that, for the most part, results in emptying of the device in random association with native heart contraction. This type of interaction between the device and assisted ventricle ignores the fact that the overwhelming majority of patients who would be candidates for mechanical assistance have at least some significant residual cardiac function.

It is preferable to allow the natural heart, no matter how badly damaged or diseased it may be, to continue contributing to the required cardiac output whenever possible so that ventricular hemodynamics are disturbed as little as possible. This points away from the use of total cardiac replacements and suggests the use of "assist" devices whenever possible. However, the use of assist devices also poses a very difficult problem: in patients suffering from severe heart disease, temporary or intermittent crises often require artificial pumps to provide "bridging" support which is sufficient to entirely replace ventricular pumping capacity for limited periods of time, such as in the hours or days following a heart attack or cardiac arrest, or during periods of severe tachycardia or fibrillation.

Accordingly, an important goal during development of the described method of pump implantation and use and of the surgically implantable reciprocating pump was to design a method and a device which could cover a wide spectrum of requirements by providing two different and distinct functions. First, an ideal cardiac pumping device should be able to provide "total" or "complete" pumping support which can keep the patient alive for brief or even prolonged periods, if the patient's heart suffers from a period of total failure or severe inadequacy. Second, in addition to being able to provide total pumping support for the body during brief periods, the pump should also be able to provide a limited "assist" function. It should be able to interact with a beating heart in a cooperative manner, with minimal disruption of the blood flow generated by the natural heartbeat. If a ventricle is still functional and able to contribute to cardiac output, as is the case in the overwhelming majority of clinical applications, then the pump will assist or augment the residual cardiac output. This allows it to take advantage of the natural, non-hemolytic pumping action of the heart to the fullest extent possible; it minimizes red blood cell lysis, it reduces mechanical stress on the pump, and it allows longer pump life and longer battery life.

Several types of surgically implantable blood pumps containing a piston-like member have been developed to provide a mechanical device for augmenting or even totally replacing the blood pumping action of a damaged or diseased mammalian heart.

U.S. Pat. No. 3,842,440 to Karlson discloses an implantable linear motor prosthetic heart and control system containing a pump having a piston-like member which is reciprocal within a magnetic field. The piston-like member includes a compressible chamber in the prosthetic heart which communicates with the vein or aorta.

U.S. Pat. Nos. 3,911,897 and 3,911,898 to Leachman, Jr. disclose heart assist devices controlled in the normal mode of operation to copulsate and counterpulsate with the heart, respectively, and produce a blood flow waveform corresponding to the blood flow waveform of the heart being assisted. The heart assist device is a pump connected serially between the discharge of a heart ventricle and the vascular system. The pump may be connected to the aorta between the left ventricle discharge immediately adjacent the aortic valve and a ligation in the aorta a short distance from the discharge. This pump has coaxially aligned cylindrical inlet and discharge pumping chambers of the same diameter and a reciprocating piston in one chamber fixedly connected with a reciprocating piston of the other chamber. The piston pump further includes a passageway leading between the inlet and discharge chambers and a check valve in the passageway preventing flow from the discharge chamber into the inlet chamber. There is no flow through the movable element of the piston.

U.S. Pat. No. 4,102,610 to Taboada et al. discloses a magnetically operated constant volume reciprocating pump which can be used as a surgically implantable heart pump or assist. The reciprocating member is a piston carrying a tilting-disk type check valve positioned in a cylinder. While a tilting disk valve results in less turbulence and applied shear to surrounding fluid than a squeezed flexible sack or rotating impeller, the shear applied may still be sufficiently excessive so as to cause damage to red blood cells.

U.S. Pat. Nos. 4,210,409 and 4,375,941 to Child disclose a pump used to assist pumping action of the heart having a piston movable in a cylindrical casing in response to magnetic forces. A tilting-disk type check valve carried by the piston provides for flow of fluid into the cylindrical casing and restricts reverse flow. A plurality of longitudinal vanes integral with the inner wall of the cylindrical casing allow for limited reverse movement of blood around the piston which may result in compression and additional shearing of red blood cells. A second fixed valve is present in the inlet of the valve to prevent reversal of flow during piston reversal.

U.S. Pat. No. 4,965,864 to Roth discloses a linear motor using multiple coils and a reciprocating element containing permanent magnets which is driven by microprocessor-controlled power semiconductors. A plurality of permanent magnets is mounted on the reciprocating member. This design does not provide for self-synchronization of the linear motor in the event the stroke of the linear motor is greater than twice the pole pitch on the reciprocating element. During start-up of the motor, or if magnetic coupling is lost, the reciprocating element may slip from its synchronous position by any multiple of two times the pole pitch. As a result, a sensing arrangement must be included in the design to detect the position of the piston so that the controller will not drive it into one end of the closed cylinder. In addition, this design having equal pole pitch and slot pitch results in a "jumpy" motion of the reciprocating element along its stroke.

In addition to the piston position sensing arrangement discussed above, the Roth design may also include a temperature sensor and a pressure sensor as well as control circuitry responsive to the sensors to produce the intended piston motion. For applications such as implantable blood pumps where replacement of failed or malfunctioning sensors requires open heart surgery, it is unacceptable to have a linear motor drive and controller that relies on any such sensors. In addition, the Roth controller circuit uses only NPN transistors thereby restricting current flow to the motor windings to one direction only.

U.S. Pat. No. 4,541,787 to Delong describes a pump configuration wherein a piston containing a permanent magnet is driven in a reciprocating fashion along the length of a cylinder by energizing a sequence of coils positioned around the outside of the cylinder. However, the coil and control system configurations disclosed only allow current to flow through one individual winding at a time. This does not make effective use of the magnetic flux produced by each pole of the magnet in the piston. To maximize force applied to the piston in a given direction, current must flow in one direction in the coils surrounding the vicinity of the north pole of the permanent magnet while current flows in the opposite direction in the coils surrounding the vicinity of the south pole of the permanent magnet. Further, during starting of the pump disclosed by Delong, if the magnetic piston is not in the vicinity of the first coil energized, the sequence of coils that are subsequently energized will ultimately approach and repel the magnetic piston toward one end of the closed cylinder. Consequently, the piston must be driven into the end of the closed cylinder before the magnetic poles created by the external coils can become coupled with the poles of the magnetic piston in attraction.

U.S. Pat. No. 4,610,658 to Buchwald et al. discloses an implantable fluid displacement peritoneovenous shunt system. The system comprises a magnetically driven pump having a spool piston fitted with a disc flap valve.

U.S. Pat. No. 5,089,017 to Young et al. discloses a drive system for artificial hearts and left ventricular assist devices comprising one or more implantable pumps driven by external electromagnets. The pump utilizes working fluid, such as sulfur hexafluoride to apply pneumatic pressure to increase blood pressure and flow rate.

SUMMARY OF THE INVENTION

This invention relates to a total artificial heart including a first surgically implantable pump and a second surgically implantable pump. Each pump includes a hollow cylinder, a piston slidably positioned in the cylinder for longitudinal movement therein, a permanent magnet member fixedly attached to the piston for movement therewith and having axially spaced magnet poles directed radially outwardly toward the outer surface of the piston, an array of electrical windings spaced axially along the hollow cylinder, and high permeability, high saturation magnetic material between the spaced electrical windings. The flux produced by the permanent magnet poles links the electrical windings. The inlet end of the tint pump is connectable to a fight atrium, the outlet end of the first pump is connectable to a pulmonary artery, the inlet end of the second pump is connectable to a left atrium and the outlet end of the second pump is connectable to an aorta. A control means for sequentially energizing the electrical windings in the array in each pump in a controlled manner so as to a oxen an axial force on the piston in each pump, causes the corresponding piston to move longitudinally through the hollow cylinder in a controlled manner in synchrony with the sequential energization of the electrical windings.

The invention also relates to a method for maintaining blood flow in a patient which includes providing a total artificial heart as described above, connecting the inlet end of the first pump to a patient's right atrium and the outlet end of the first pump to a patient's pulmonary artery, and connecting the inlet end of the second pump to a patient's left atrium and the outlet end of the second pump to a patient's aorta.

BRIEF DESCRIPTION OF THE DRAWINGS

Further objects and advantages of the invention will be apparent from a reading of the following description in conjunction with the accompanying drawings, in which:

FIGS. 7(a)–7(j) are fragmentary cross-sectional views illustrating the stages in the energization of the coils of a linear motor drive in accordance with the invention;

DESCRIPTION OF PREFERRED EMBODIMENTS

Figure 1:
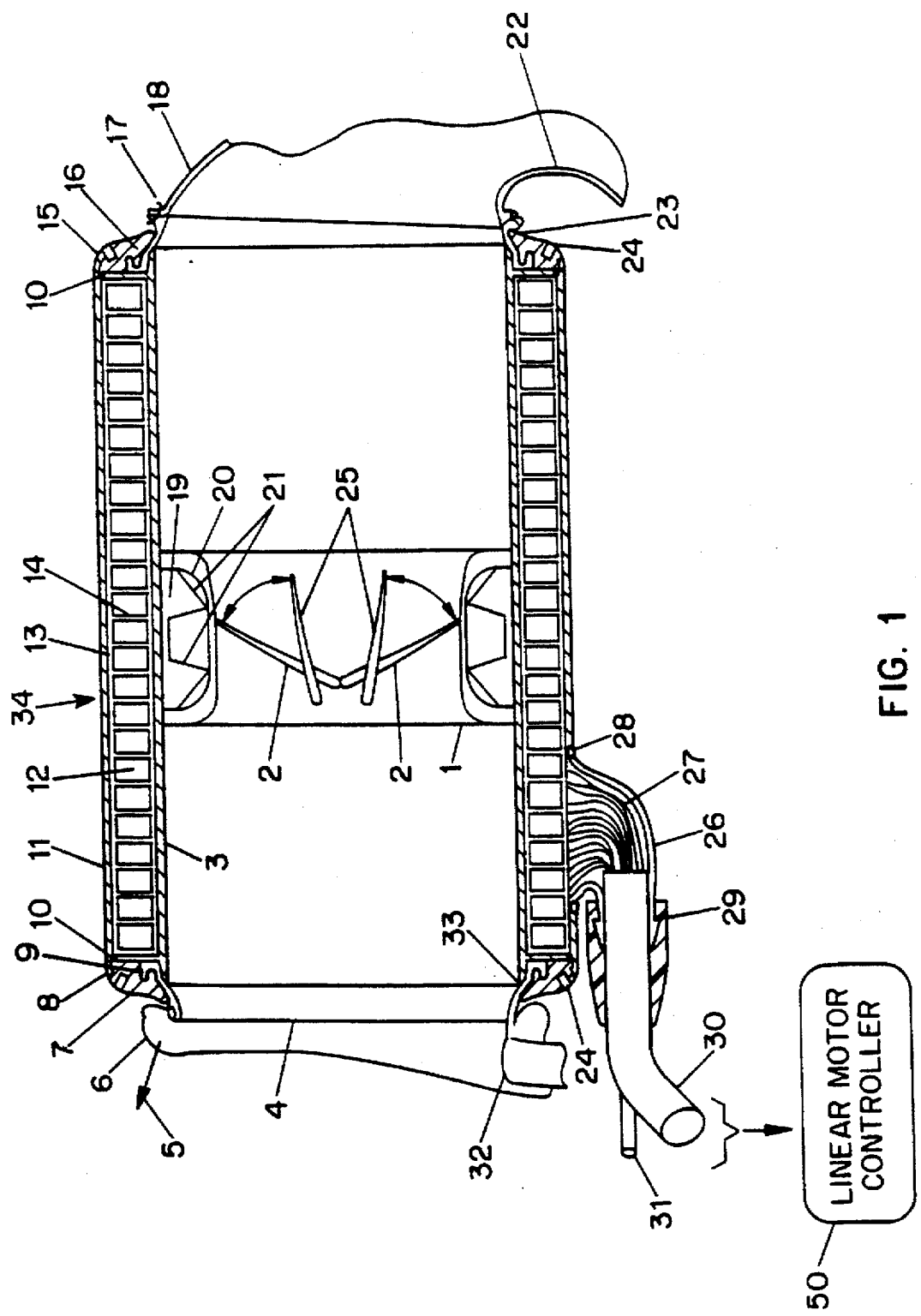
FIG. 1 is a longitudinal sectional view illustrating a representative surgically implantable pump with a reciprocating piston-valve arranged in accordance with the invention.

In the representative embodiment of a pump according to the invention as shown in FIG. 1, a pump module arrangement 34, which is for example, no more than 6 cm in diameter and 7.5 cm long, includes a reciprocating piston-valve assembly 1 consisting of an annular piston with a central flow passage containing two pivoting valve leaflets 2 which act as a check valve to limit flow through the central passage during reciprocation to one direction only. The piston-valve assembly 1 is driven back and forth through an internal cylinder 3 in the pump module 34 to displace fluid from an inlet end to an outlet end. Smooth and vibration-free motion can be ensured by providing close-clearance, low friction interfaces between the cylinder inner diameter and the piston-valve.

The piston-valve 1, leaflets 2 and internal cylinder 3 are all preferably fabricated from highly corrosion-resistant material such as titanium or carbon, and are coated with low-friction, wear-resistant, non-thrombogenic material. One material which has been shown to have a good combination of biocompatibility and high strength is pyrolytic carbon, which is used to coat the housing and leaflets of various types of prosthetic heart valves, such as the St. Jude valve. The coating can be applied by a conventional vapor deposition process, resulting in a layer containing about 90% carbon and 10% silicon on the surface of a graphite structure.

When used as an implantable left ventricular assist device (LVAD), the pump module 34 is attached at its inlet end using a sewing cuff 4 to a patient's aorta 5 immediately downstream of the aortic valve (not shown in FIG. 1) using a suture 6. In this manner, the patient's own normally functioning aortic valve precludes back-flow of blood into the patient's left ventricle when the piston-valve makes its return stroke. Preferably the sewing cuff 4 is made from a synthetic surgical graft material such as woven Dacron™ available from the Dupont Corporation. The sewing cuff 4 can be attached to the LVAD using a retaining ring 7 which snaps into cantilevered barbs 8 or other similar retaining arrangements. The sewing cuff has an enlarged end 9 which becomes physically captured or entrapped by the retaining ring 7 when it is snapped into place. Compression of the sewing cuff 9 by the retaining ring 7 against the cylinder 3 forms a hemostatic seal.

At the outlet end of the cylinder 3 a retaining ring 15 is used in conjunction with a sewing cuff 16 in a similar manner as described herein above. The sewing cuff 16 is attached using a suture 17 to the patient's distal ascending aorta 18.

If the pump is to be inserted directly into an artery, the sewing cuffs 4 and 16 should be relatively short, such as about 2 cm or less in length. If the pump is designed for insertion in any other manner, such as for direct left atrial-to-aortic ventricular assistance in which an opening is cut into a wall of the left atrium and directly into the aorta, bypassing the left ventricle, the sewing cuffs should be substantially longer, such as about 30 cm or more at each end so they can be cut to any designed length by a surgeon without requiring an additional suturing procedure for an attachment cannula.

Figure 2:
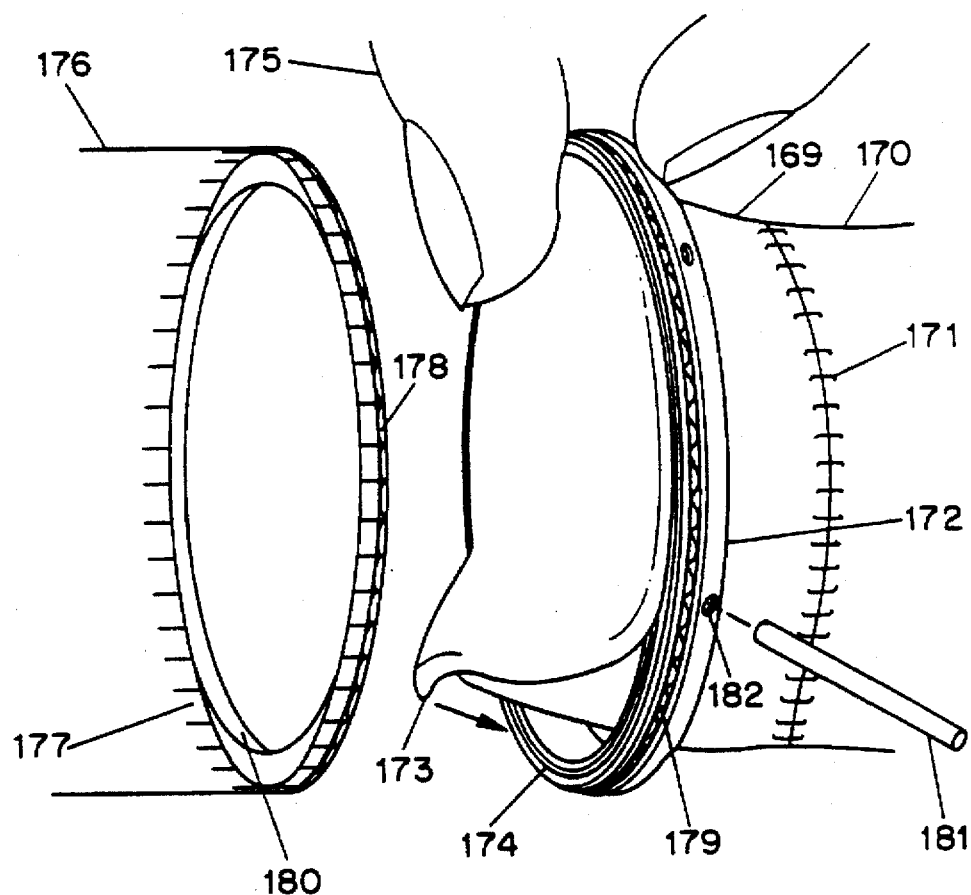
FIG. 2 is a perspective view illustrating a representative arrangement for attachment of vascular grafts to a surgically implantable pump in accordance with the invention.

FIG. 2 depicts a method and arrangement for attachment of vascular grafts to a surgically implantable pump module 176. A graft 169 is sewn to a patient's native vessel 170 using a suture 171. The suturing is performed prior to the installation of a retaining ring 172 which is not permanently attached to the graft 169, thereby avoiding obstruction by the retaining ring while suturing. The retaining ring 172 is installed onto the graft 169 after suturing is completed by slipping the retaining ring over the flexible graft and inserting an enlarged lip 173 of the graft into a recessed groove 174 using the thumb and forefinger 175 as shown. The enlarged lip may optionally be seated against a simple shoulder inside the retaining ring, instead of the recessed groove 174. After the graft is properly seated in the retaining ring 172, a pump module 176 is fastened to the retaining ring using cantilevered springs 177 extending from the pump module 176 which incorporate barbs 178. These barbs seat and lock axially into mating recesses 179 machined into the retaining ring 172. Alternate fastening arrangements may also be used such as a "bayonet" type connection, which is commonly used in cylindrical electrical connectors and involves the use of locking cams and spring loaded followers. Once seated, the graft forms a hemostatic seal around a hollow extension 180 of the internal cylinder in the pump module. The retaining ring can be removed by inserting a bar 181 or other engaging device into equally-spaced holes 182 in the ring and rotating the ring 172 slightly. For the fastening arrangement shown, this will cause the barbs 178, which are rounded when viewed in a circumferential cross-section, to ride up and out of the recesses 179, disengaging the axial locking feature and permitting the retaining ring to be removed. Instead of the bar 181, a more sophisticated spanner wrench type tool can be used.

Figure 2A:
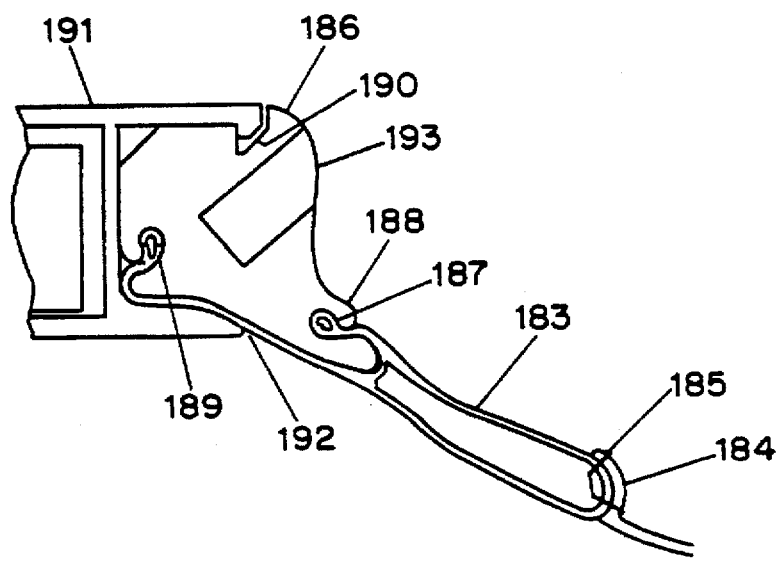
FIG. 2(a) is an enlarged fragmentary view illustrating another alternative arrangement for attachment of the pump to a blood vessel.

An alternate graft configuration is shown in FIG. 2(a). In this case, a sewing ring 183 is attached to an artery 184 using a two-layered suturing technique (not shown). The cuff is filled with foam or other filler material to ease suture attachment by producing a thicker graft as shown. The graft 183 can be directly attached to a retaining ring 186 or, if desired, it can be attached to the retaining ring by an intervening thinner graft material 169 of the type shown in FIG. 2. Conversely, a thicker graft 183 may be attached by using an enlarged lip of graft material 173 inserted into a groove similar to the groove 174 shown in FIG. 2 if access to a suture line 185 is considered to be inadequate with the retaining ring 186 preattached to the graft 183. In one method of attaching the graft 183 to the retaining ring 186, an enlarged lip 187 of the graft is inserted into a groove 188 machined in the retaining ring and then mechanically rolled within the groove which physically captures the end of the graft. A similar enlarged lip 189 can be rolled within a groove on the inside of the retaining ring. An alternate method of attaching the graft such as a separate metallic ring compressed around the graft may also be used instead of the rolled-over lips 187 and 189.

The retaining ring 186 has a series of recesses 190 shaped to conform to the inside surfaces of barbed cantilevered springs 191. The sectional view of FIG. 2(a) shows a spring 191 and a recess 190 corresponding to the springs 177 and recesses 179, discussed above with respect to FIG. 2, by which the retaining ring is assembled to the pump module. The clearance between the retaining ring 172 or 186 and the pump module when they are assembled is such that the spring 177 or 191 presses radially inwardly and slightly axially on the retaining ring, thereby compressing the graft 173 or 183 against the inner cylinder extension 180 or 192 to form a hemostatic seal. As in the embodiment of FIG. 2, the recesses 190 are shaped so that the retaining ring 186 can be released by inserting a tool in one or more equally spaced holes.

Figure 3:
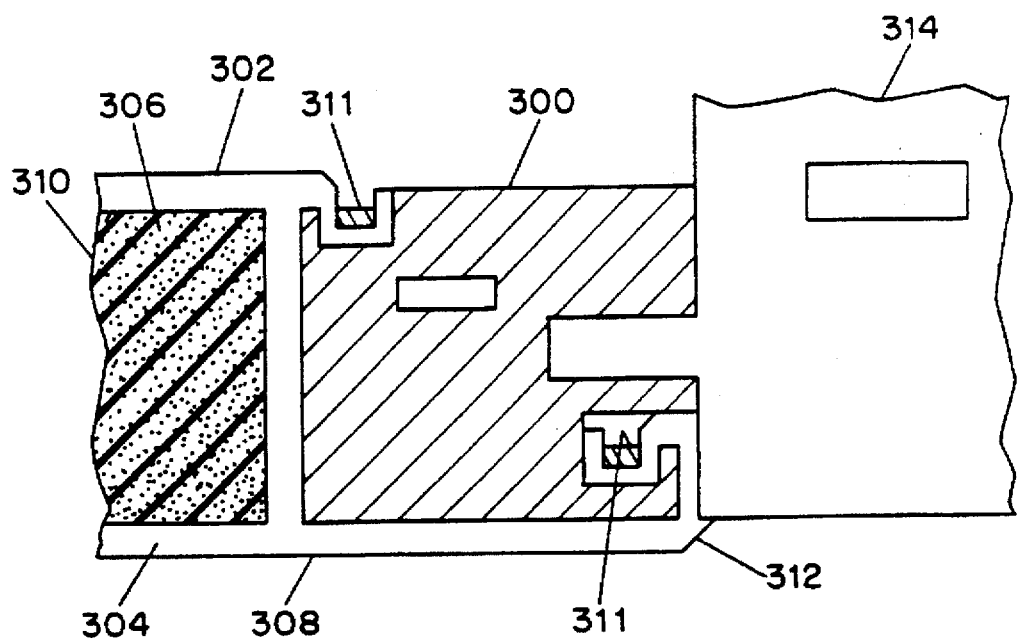
FIG. 3 is an enlarged fragmentary sectional view illustrating a representative quick connect locking system for attaching a surgically implantable pump with a blood vessel arranged in accordance with the invention.

In another preferred embodiment, the aorta-pump connection is obtained using a quick connect locking system as shown in FIG. 3. The quick connect locking system comprises a metal ring 300 of titanium or other suitable metal and a sewing ring 302. The sewing ring includes a dacron endothelial promoting outer covering 304 and compliant foam rubber inner part 306. One end 308 of the sewing ring 302 is attached to the metal ring 300 by any connecting arrangement compatible with human implantation, for example, by internal circumferential fastener bands 311. The metal ring 300 is, in turn, coupled to a pump module 314 by one of the quick connect locking mechanisms of the type discussed above which is shown schematically in FIG. 3. The other end 310 of the sewing ring 302 is sutured to the aorta in the usual manner. The suture connection anastomosis will smooth over with time as endothelium from the native aorta extends over the outer covering 304. The endothelial overgrowth 312 will also extend over the junction of the quick connect locking mechanism.

Returning to the pump arrangement shown in FIG. 1, a high energy density rare earth permanent magnet 19 having axially spaced north and south pole pieces 21 is mounted on the circumference of the piston-valve 1. A hermetically sealed enclosure 20 made from a highly corrosion-resistant material such as titanium surrounds the permanent magnet 19 and its pole pieces 21. Preferably, the high energy density rare earth material is neodymium-iron-boron. The pole pieces 21, which are made from soft ferromagnetic material, direct the magnetic flux so as to project outward radially from the axially oriented permanent magnet toward the circumference of the piston-valve. The radial magnetic flux thus intercepts the windings 12 of a linear motor that surrounds the cylinder 3 through which the piston-valve 1 slides, the windings being formed in slots separated by magnetically soft lamination material 14 of the type commonly used in commercial motors, generators and transformers. A magnetically soft backing 13 surrounds the winding slots to provide a low reluctance path for the flux generated by the piston-valve magnet to link the windings. The laminations are positioned so as to avoid slot harmonics which would cause non-uniform motion of the piston-valve and are sized to minimize the effective air gap across which the magnetic flux must pass. Particularly smooth motion is obtained by using odd/even ratios of winding slot pitch to magnetic pole pitch on the piston-valve, respectively, or vice versa. In this regard, multiple phase windings are required.

The linear motor windings and laminations are encased in a corrosion-resistant enclosure which includes a hermetically sealed penetration 26 for a linear motor lead bundle 30 leading to a linear motor controller 50 described hereinafter. This bundle further includes a pair of epicardial sensing leads 31. A seal weld 10 is provided at each end of the pump module 34 to form a hermetic seal between an outer housing 11 for the pump and the inner cylinder 3. The hermetic seal prevents moisture or other contaminants from attacking the linear motor windings 12, back iron material 13 or lamination material 14.

Suitable voltage is provided to the windings of the linear motor by wires in the bundle 30 which are connected to a battery associated with the controller 50. The wires which supply power to the motor are positioned outside the aorta and thus do not contact blood flowing through the aorta.

The outer housing 11 can be composed of any suitably hard biocompatible material, such as titanium, stainless steel, various other alloys, graphite, or plastic. It can be sealed with a standard waterproof epoxy coating.

In operation, as the piston-valve 1 moves toward the outlet end of the pump, i.e., the right end as viewed in FIG. 1, fluid on the downstream side of the piston-valve is ejected from the outlet end due to the fact that the piston-valve leaflets automatically move to their closed position 2 from their open position 25 shown in dotted lines when the piston-valve moves with respect to the fluid in the pump toward the outlet end of the pump or when fluid attempts to flow past the piston-valve in the direction toward the inlet. As the piston-valve 1 reaches the outlet end of its pumping stroke, its direction of travel is reversed by the controller 50 and, as the piston-valve begins its travel back toward the inlet end of the cylinder, i.e., the left end as viewed in FIG. 1, the piston-valve leaflets automatically move to the open position 25, allowing the fluid to flow from the upstream side of the piston-valve to the downstream side of the piston-valve as it moves along the cylinder.

If the linear motor malfunctions and attempts to drive the piston-valve beyond the ends of the cylinder 3, the retaining rings 7 and 15 are shaped so as to prevent the piston-valve from moving past the sewing cuffs 4. As another back-up mechanism, the shape of the retaining rings 7 and 15 is arranged so that the piston-valve will not become jammed in the sewing cuff or damage the sewing cuff in any way. In the outlet end of the pump used as a LVAD, a patient's aorta 32 bends sharply at the aorta arch 22. To smooth out the flow path, the retaining ring 15 may have a trimmed portion 23 at this location as shown in FIG. 1. The retaining rings 7 and 15 preferably have at least four equally spaced tool holes 24 to receive a tool for removing the retaining rings after they have been snapped into place as described above.

In LVAD applications, where the pump is positioned in the outflow duct of the left ventricle, the pump inlet is downstream of the left and right coronary artery ostia or openings. During normal operation, the piston travels back from the outlet end of the cylinder as slowly as possible during the patient's native heart diastole so that it arrives at the inlet end of the cylinder just before the patient's left ventricle begins to eject blood during systole. This ensures that the patient's coronary artery 32 receives adequate blood flow during diastole, when most of the blood that normally enters the coronary arteries is actually admitted. The slow motion of the piston-valve back toward the inlet end of the cylinder also limits shear stress in the blood flowing to the downstream side of the piston-valve and should result in a slight increased pressure at the inlet to the patient's coronary arteries, which will improve blood flow to the patient's native heart muscle during diastole. This is expected to compensate for the possibly slightly reduced pressure at the inlet to the patient's coronary arteries that will occur during systole caused by the pumping action of the piston-valve moving toward the outlet end of the cylinder. A seam 33 formed at the interfaces between each of the sewing cuffs 4 and 16 and the hollow cylinder 3 is compressed against the cylinder by the retaining rings 7 and 15. This ensures that the crevice formed at the seam will become covered with a smooth secure endothelial layer to preclude formation and release of blood clots in this area.

The hermetically sealed cable penetration 26 which is made from a highly corrosion-resistant material such as titanium houses the linear motor winding leads 27 and is seal welded to the outer housing 11. The main lead bundle 30 contains a shielded multi-conductor cable with a polyurethane jacket material similar to insulation currently used for pacemaker leads. Such cable is commercially available for machine tool and robotics application, and is rated in excess of 6 million bend cycles from straight to its minimum bend radius without failure of the insulation or conductors. The main lead bundle incorporates approximately 24 conductors required to drive the linear motor in VAD applications. The main lead bundle terminates at a hermetically sealed cylindrical connector at the linear motor controller 50. A molded polyurethane strain relief 29 attaches the polyurethane jacket of the shielded multi-conductor cable 30 which constitutes the main lead bundle to the linear motor to the cable penetration. An optional second strain relief attached to the polyurethane jacket includes the leads 31 which are routed to epicardial electrodes used to provide an ECG signal to the linear motor controller 50.

Figure 4:
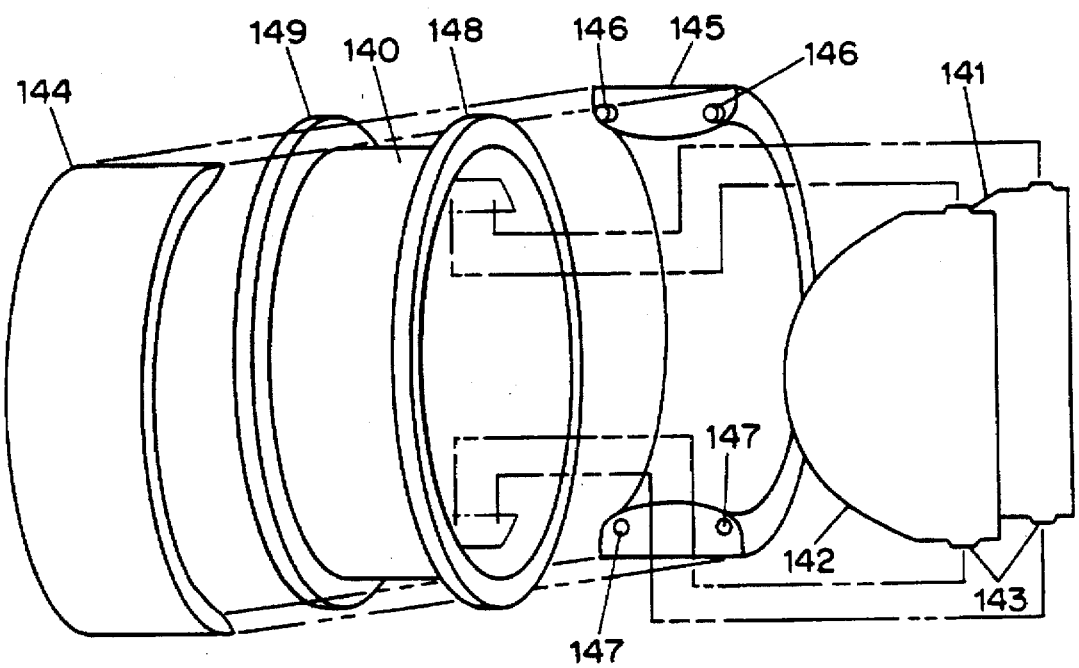
FIG. 4 is an exploded perspective view showing the arrangement of a typical piston-valve for use in a surgically implantable pump in accordance with the invention.

FIG. 4 shows a representative piston-valve structure for use in the surgically implantable pumps discussed herein. The piston body has a main carrier 140 constructed of a light weight wear- and corrosion-resistant material such as titanium, silicon carbide or graphite, appropriately coated with a biocompatible material such as pyrolytic carbon. For the simplex TAH embodiment shown in FIG. 17, the piston body has a carrier which is solid, whereas in the embodiment shown in FIG. 4 the carrier 140 has a central opening in which valve leaflets 141 and 142 are inserted to form a check valve similar to those used for prosthetic heart valves. To support the leaflets 141 and 142, the carrier opening has small depressions into which leaflet hinge tabs 143 are inserted by thermally or otherwise expanding the carrier such that the tabs 143 will clear the inner dimensions of the orifice, and then allowing the carrier to contract around the leaflets, resulting in mechanical retention of the tabs in their corresponding depressions.

The magnet assemblies 144 and 145 are preferably mounted around the carrier 140 after the leaflets 142 and 143 are installed. This avoids exposure of the magnets to the potentially high temperatures which may be experienced during leaflet insertion or application of the biocompatible coating which may be pyrolytic carbon. Each magnet assembly contains one or more high energy density permanent magnets, and appropriate pole pieces to direct the flux outward radially, all hermetically sealed within a corrosion-resistant covering. Each magnet assembly consists of two halves 144 and 145 provided with insertion studs 146 and stud receivers 147 or other arrangements for fastening the two magnet assembly halves securely around the carrier when they are pressed together. A biocompatible adhesive compound may also be used to provide additional security to the assembly of the magnet halves 144 and 145. When assembled to the carrier 140, the outer surface of the magnet halves 144 and 145 is slightly recessed with respect to the outermost rim surfaces 148 and 149 of the carrier. This ensures that only the surfaces 148 and 149, which are precision machined wear surfaces, are in contact with the cylinder walls of the pump module as the piston travels through its stroke.

Figure 5:
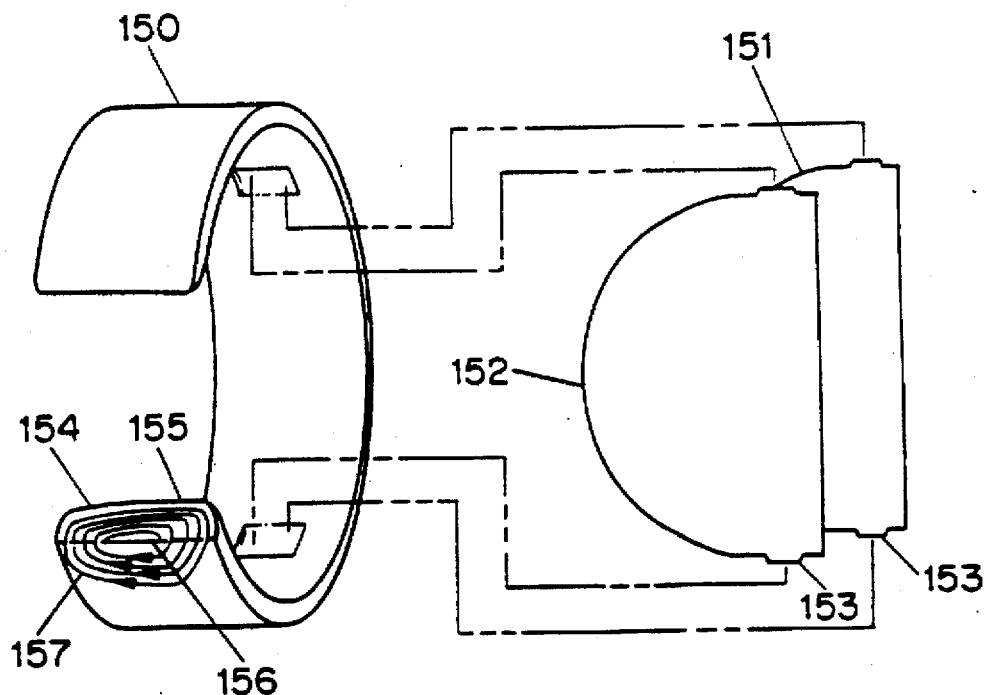
FIG. 5 is an exploded view showing an alternate configuration for assembling a piston-valve for use in a surgically implantable pump in accordance with the invention.

FIG. 5 shows an alternate embodiment of a piston-valve assembly. In this embodiment, a carrier 150 is solid and has a central opening as shown for insertion of valve leaflets 151 and 152, or other arrangements to form a valve similar to conventional prosthetic heart valves. The leaflets incorporate tabs 153 to be inserted into corresponding depressions in the central opening of the carrier by thermally or otherwise expanding the carrier. In this piston configuration, two magnets 154 and 155 are incorporated into the carrier and are manufactured to have the desired shape of the carrier, less the biocompatible coating. A spacer 156 may also be included to produce the desired carrier shape. The magnets are preferably oriented to provide the required flux pattern 157 so that pole pieces are not required. Although this piston-valve configuration may require that the magnet material be exposed to the high temperatures potentially experienced during coating application and leaflet insertion, the magnet material should not lose its preferential grain orientation provided the sintering temperature of the magnetic material is not exceeded. If the Curie temperature of the magnet material is approached or exceeded, however, the magnet may require remagnetization.

Figure 6:
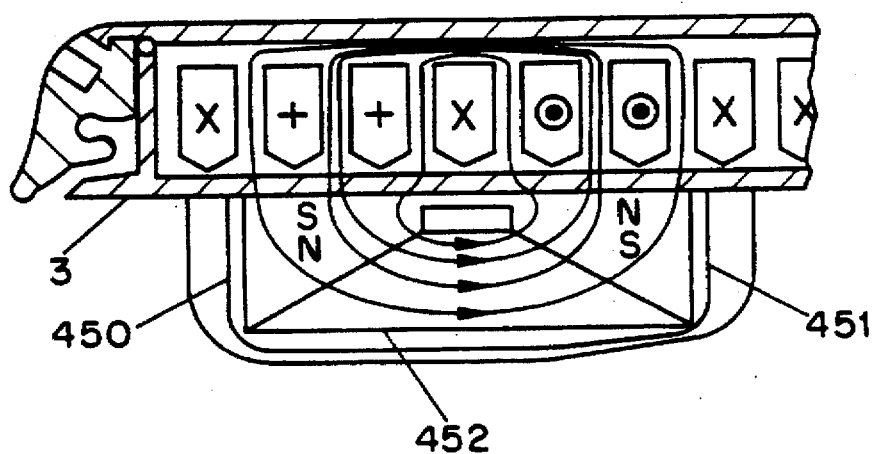
FIG. 6 is a fragmentary cross-sectional view showing an alternate magnet arrangement for use in a surgically implantable pump in accordance with the invention.

An alternate arrangement of the permanent magnets used in the pistons shown in FIGS. 1, 4 and 5 is shown in FIG. 6. In this arrangement, two annular permanent magnets 450, 451 have a radial magnetic pole orientation. A magnetically soft ferromagnetic material 452 such as iron-cobalt material couples the poles on the inner surfaces of the annular magnet to provide a low reluctance path for the flux passing through the outer surfaces of the permanent magnets.

The operation of a linear motor pump module in accordance with the invention is described hereinafter in greater detail with reference to FIGS. 7(a)-7(j) which show a diagrammatic cross-section of the linear motor drive for the pump module. In these views, a piston 194, containing a magnet assembly 195 is free to slide through a cylinder 196 as previously discussed. Magnetic flux 197 generated by the magnet assembly 195 is made to link several of the windings 198 by the magnetically soft radial laminations 199 and circumferential laminations 200, which separate and surround the windings 198. The laminations 199 and 200 can be manufactured from thin sheets of material such as silicon iron or iron-cobalt bonded together to the proper thickness to accommodate the magnetic flux produced by the magnet 195. The radial laminations 199 also include an axially enlarged portion near the outer surface of the inner cylinder 196 to improve magnetic coupling between the piston magnet 195 and the windings. This enlargement may not be necessary if the motor performance otherwise satisfies the operation requirements.

FIG. 7(a) shows the piston 194 at the inlet end of the cylinder 196 with a series of windings 601–623 having energization leads 501–526 with the first five windings 601–605 all energized by current flowing in the same direction, i.e., into the plane of the drawings, represented by the symbol "+", and all other windings 606–623 with no current represented by "×". This current is produced by the "high" potentials applied at the leads 501 and 502 (e.g., 12 volts, designated by "H") and the "low" potential applied at the leads 507 and 508 (e.g., 0 volts designated by "L"). All other leads are connected to an open circuit (designated by "×"). This energization pattern provides a holding mode to hold the piston 194 in a given position in the cylinder 196 until the next pumping or return stroke is initiated. Current through the windings at this stage is limited to a nominal level using pulse width modulation (PWM) or another efficient current limiting method to avoid excessive winding heating and power consumption.

FIG. 7(b) shows the piston 194 at the inlet end of the cylinder with the first five windings 601–605 of the series of windings 601–623 energized to begin a pumping stroke. For this purpose, the windings 601 and 602 are energized with current flowing into the plane of the drawing "+" while the windings 604 and 605 are energized with current flowing out of the plane of the drawing, represented by "⊙". Given the orientation of the magnetic flux from the magnet 195 and the current in the energized windings, a force will be exerted on the piston driving it to the right. The controller 50 includes a current limiting arrangement to prevent damage to the windings as discussed earlier, but such current limitation is not expected to be required once the piston begins to move along the cylinder and generate a counter emf.

Figure 7C:
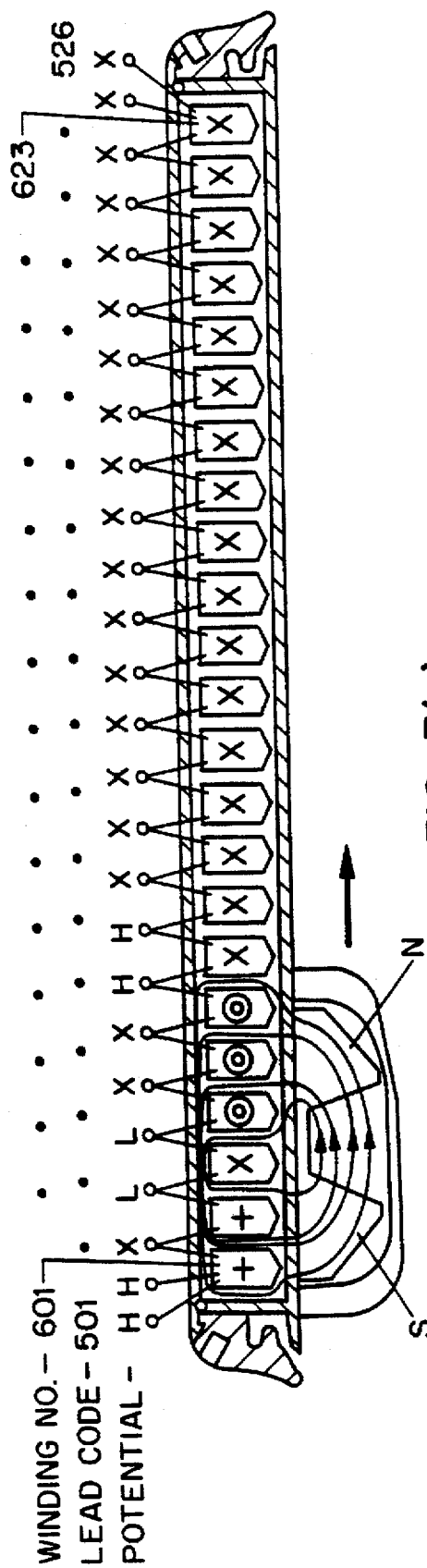
Figure 7D:
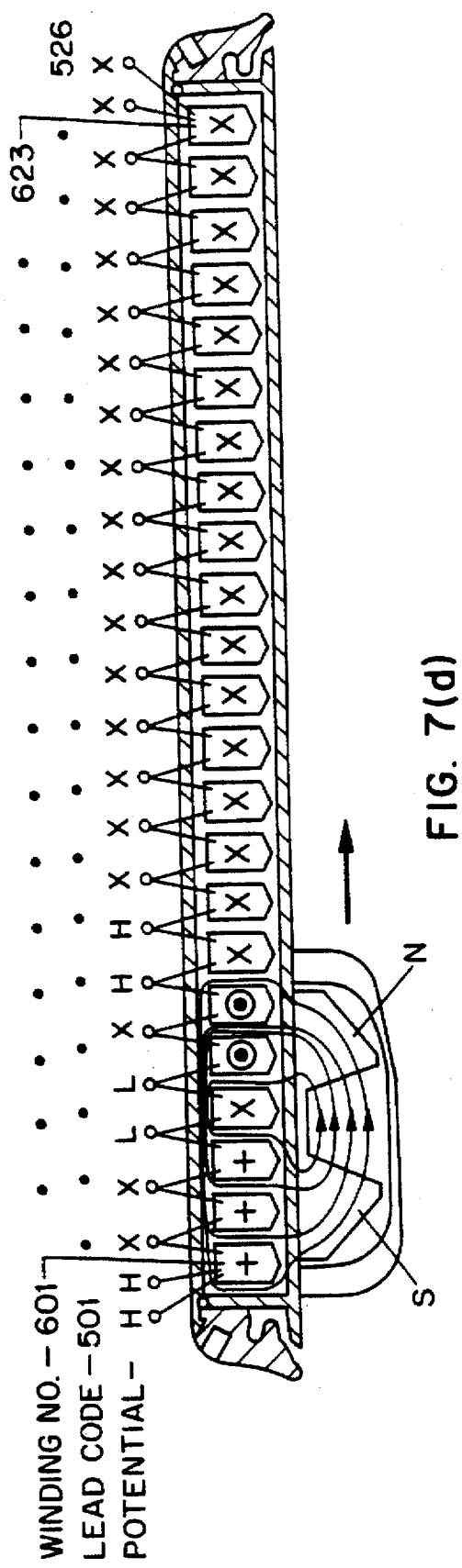
Figure 7E:
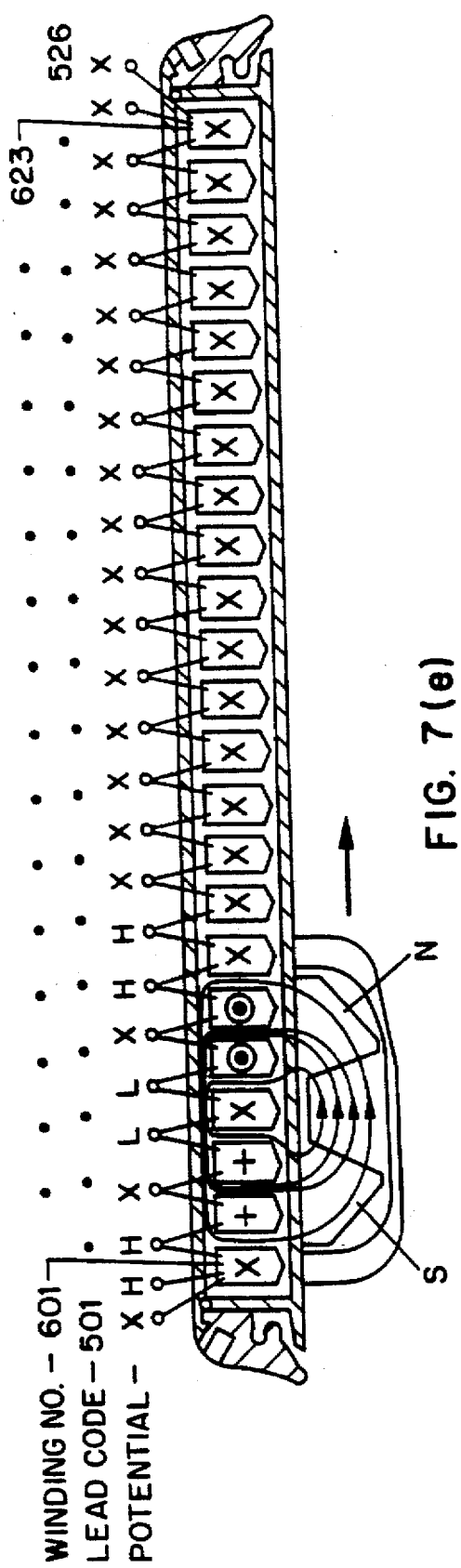
Figure 7F:
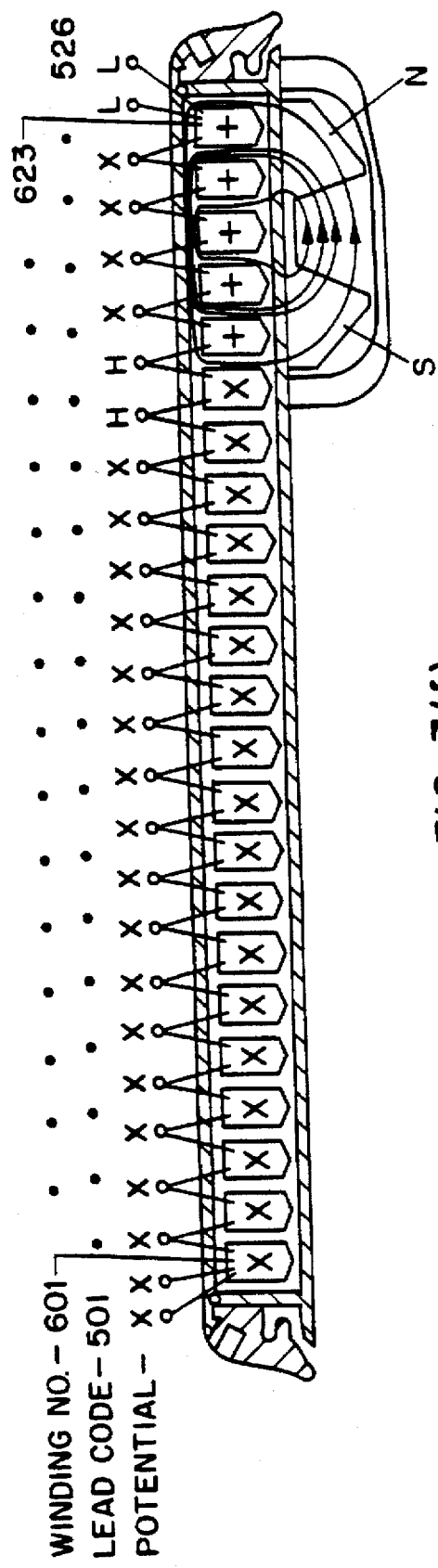
Figure 7G:
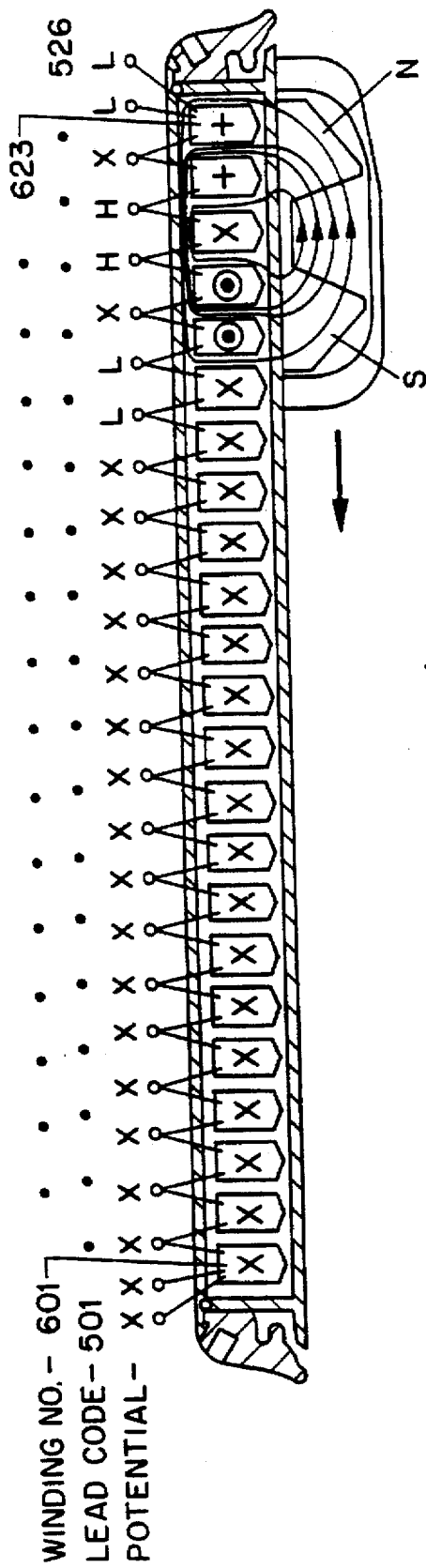

FIG. 7(c) shows the piston 194 progressing to the right. In this case, the winding 606 has been energized in the same direction as the windings 604 and 605 in anticipation of the leading edge of the magnet beginning to couple this winding. FIG. 7(d) shows a further progression of the piston to the right with the winding 603 energized like the windings 601 and 602 and the winding 604 being de-energized. All of the windings 601–623 are connected in series which allows the inductive flyback energy released when a winding such as the winding 604 is de-energized to be usefully transferred into the neighboring windings rather than being dissipated wastefully through the controller circuit. FIG. 7(e) shows the piston progressing still further along its stroke with the winding 601 now de-energized. The pattern of windings energized is now the same as it was in FIG. 7(b), except offset to the right by one winding. The pattern described by FIGS. 7(b) through 7(e) repeats until the piston reaches the end of its stroke, where it may be held momentarily as shown in FIG. 7(f). The pattern then begins again, except with current directions in the windings reversed, when the piston is driven back toward the inlet end of the cylinder as shown in FIG. 7(g).

In the arrangement shown in FIGS. 7(a)–7(j) the magnet pole pitch is not equal to an integral multiple of the winding slot pitch. This requires an out of phase energization of the coils which are being approached by the leading edge of the north pole of the magnet in contrast to those being approached by the south pole of the magnet. Although this complicates the timing used in the control circuit, the movement of the piston is smoother along its stroke when the energizing of approaching windings is divided into multiple transitions for a given displacement instead of one.

The timing used in the control circuit for the motor could be simplified if desired if both the magnetic pole width and the pole pitch were made equal to an integral multiple of the winding slot pitch. With this arrangement, the windings being approached by the leading edges of both magnetic poles can be energized at the same time that the windings being left behind by the trailing edges of both magnetic poles are de-energized. However, the piston will tend to move forward abruptly each time this combination of simultaneous energizing and de-energizing at multiple windings occurs. This would be undesirable for applications such as implantable circulatory assist devices where uniform motion of the piston is required to minimize vibration and high frequency pulsation of the fluid that could cause unnatural sensations. The most uniform motion of the piston can be obtained by making both the width and pitch of the magnetic poles unequal to an integral multiple of the slot pitch. This also results in the most complicated timing in the control circuit. In this case, the timing sequence proceeds as follows: the winding being approached by the leading edge of the first magnet pole is energized, then the winding being left by the trailing edge of the second magnet pole is de-energized, then the winding being left by the first pole is de-energized, then the winding being approached by the second pole is energized, and so on. However, with large scale programmable logic devices such as microcontrollers, programmable gate arrays, etc., it is possible to implement such complex winding energization timing algorithms without much difficulty.

Figure 7H:
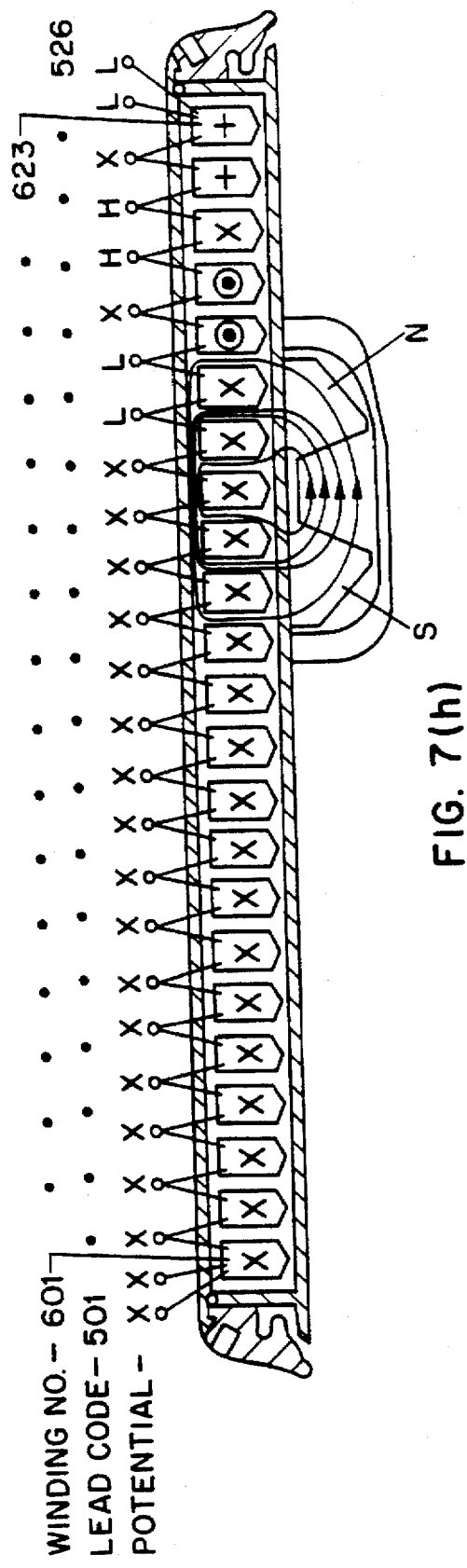

It can be seen from FIG. 7(h) that the piston position will be automatically synchronized with the pattern of windings being energized during initial start-up of the motor, or if magnetic coupling between the piston and the windings is lost for some reason, without the piston ever being driven into the travel stops at the end of the cylinder. As shown in FIG. 7(h), the pattern of energized windings is initially that shown in FIG. 7(g). As the pattern of energized windings shown in FIG. 7(g) progresses to the left, it will approach the stationary piston in the middle of the cylinder. As the windings at the leading edge of the pattern of energized windings begins to interact with the flux emanating from the north pole of the stationary piston, as shown in FIG. 7(i), the piston will experience a force drawing it to the right, into the pattern of energized windings, even though the pattern is moving to the left. This is because the leading windings would normally act on the flux entering into the south pole of the piston magnet, which would cause the piston to experience a force drawing the piston to the left. The opposite direction of the magnetic flux emanating from the north pole causes the force acting on the piston to be reversed. The piston will continue to be drawn to the right until it becomes centered in the pattern of energized coils, as shown in FIG. 7(j), which is its normal synchronous position. Because of the energization pattern, it will continue, from that point on, to move synchronously in the same location with respect to the pattern of energized coils. This process of resynchronization will take place as long as the piston is anywhere within the travel limits of the cylinder which is physically ensured as long as end connections such as those depicted in FIGS. 2, 2(a) and 3 are provided.

It can also be seen that failure of a single lead in the series 501–526 will have no effect other than possibly to add an additional winding to the circuit that would not normally be energized. Referring to FIG. 7(b), if the lead 507 were to fail, the winding 606 would become energized in the direction ⊙, providing current out of plane of the drawing, which would have little effect on motor operation other than a slightly increased winding impedance. The same can be said for any other failure of an active lead for the pattern of lead potentials shown in FIG. 7.

A fault detection algorithm can be incorporated into the controller 50 for the linear motor drive by using a current sensor that provides a signal representing total current flowing through the motor windings to the controller logic circuit, which compares this value to an expected value or an average of previous values for the active set of windings. Any discontinuity as a result of a change in winding impedance due to a failed lead will be manifested as a departure from the expected or time averaged current level as the failed lead is energized. The fault can then be annunciated by the controller so that corrective action to repair the failed lead can be taken before a complete malfunction of the motor occurs.

The controller 50 can also be programmed to detect and flag a failed winding by monitoring for the associated discontinuity in electric current to the motor. The failed winding can then be selectively skipped over on subsequent cycles so that only one (i.e., the failed winding) out of the four or five windings in the pattern of energized windings influencing the piston at any one time will be lost. Further, the remaining windings may carry slightly greater current to compensate for the failed winding with no other adverse effects with the exception of slightly decreased efficiency and slightly increased winding operating temperature.

Referring to FIG. 7(c), if the winding 606 were to fail, then no current could pass from the leads 508 and 509 to the lead 505, but the windings 601 and 602 would still remain energized by the leads 501, 502 and 504. The current would be limited to these windings by the back emf generated by the moving magnetic pole or by the PWM current limiting feature discussed above. A motor designed for high reliability will incorporate windings rated to handle twice the normal current and permanent magnets that will not be demagnetized by this doubling of current so that a single failed winding will not cause a complete malfunction of the motor. Additionally, the motor controller 50 can be designed to detect a failed winding using an algorithm similar to that described above for detecting a failed lead, so that replacement of the motor can be accomplished before a complete malfunction occurs. A further improvement of the failed winding detection algorithm would be to use the magnitude of the current discontinuity detected by the controller 50 to distinguish between a failed lead 501-526 and a failed winding 601-623. This is advantageous for determining whether the pump module 34 must be replaced (i.e., due to winding failure) or possibly only the controller 50 must be replaced (i.e., due to a lead failure near or within the controller). This failed winding detection algorithm can be yet further enhanced by modifying the timing of lead potentials applied to the motor when a failed winding is identified such that only that winding is lost from the desired pattern of windings to be energized. For instance, referring to FIG. 7(b), if the winding 606 has been identified as a failed winding as described above, the controller 50 will maintain a high potential on the lead 507 in FIGS. 7(c), 7(d) and 7(e), instead of isolating current flow to this lead. A low potential will be applied to the lead 507 when this would normally have occurred in a subsequent transition of lead potentials. However, a low potential will also be applied to the lead 508 on the other side of the failed winding 606 at that time to maintain a current path on either side of the failed winding. A similar scheme will be used as the south pole of the piston magnet 195 passes by the failed winding except that the lead potentials will be reversed. This modification of the winding energization timing will ensure that all windings with the exception of the failed winding will receive electric current according to the desired timing sequence.

Figure 8:
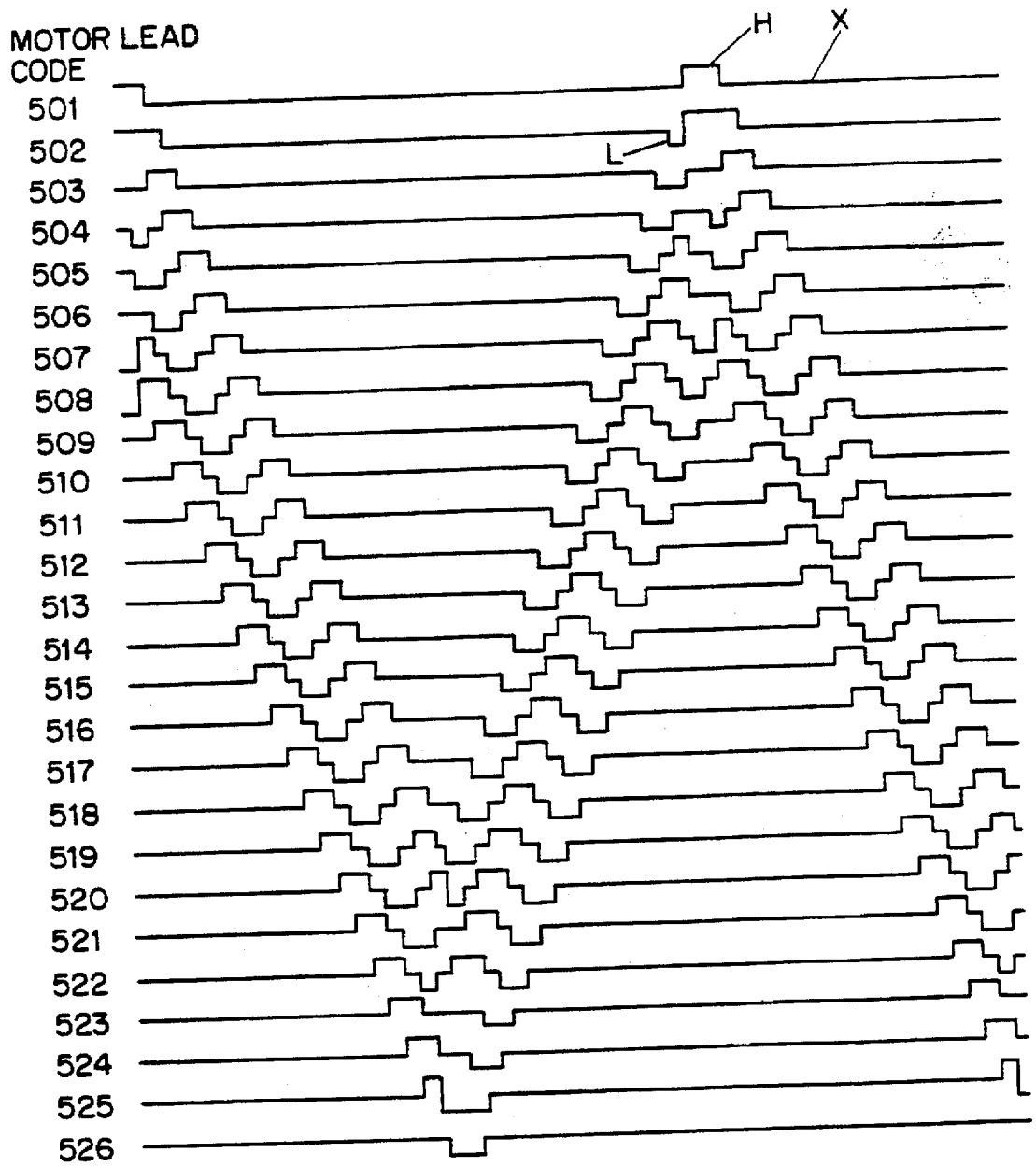
FIGS. 8 and 8(a) are graphical representatives showing the timing of the application potential to the coils of the linear motor of FIG. 1 in accordance with the invention and a typical electrocardiogram signal respectively.

FIG. 8 comprises a series of timing diagrams that show the successive lead potentials required at the leads 501-526 to produce the normal pattern of energized windings described in connection with FIG. 7(a)-7(j). A typical ECG signal is also shown in FIG. 8(a).

Figure 8A:
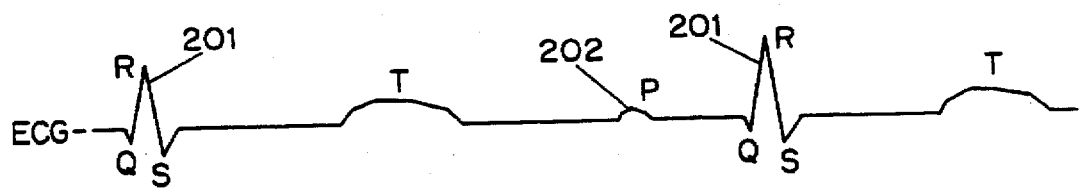

The ECG signal shown in FIG. 8(a) illustrates the P, Q, R, S and T waves. This is an electrical signal generated by the heart and is sensed by ECG leads attached to the inner (endocardial) or outer (epicardial) surface of the heart muscles or may also be sensed on the outer surface of the body. The P wave is caused by the spread of depolarization of the atrial muscle, which initiates contraction of the atria. Approximately 0.16 seconds after the onset of the P wave, the QRS waves appear as a result of depolarization of the ventricular muscle, which initiates contraction of the ventricles. Finally, the T wave results from repolarization of the ventricles, which represents the onset of ventricular relaxation. The optimum starting point for the winding energization timing cycle in VAD applications to begin is expected to be on or about the R-wave peak 201. This peak value shown in FIG. 8(a) typically occurs just before the recipient's aortic (or pulmonary) valve would normally be pushed open by blood being ejected from the native left (or right) ventricle. For TAH applications, the entire QRST complex will be missing from the ECG signal. Therefore, the timing cycle shown will have to be initiated at some predetermined delay interval referenced to the P-wave peak 202 generated by the recipient's native sinus node. This predetermined delay interval will be a programmable setting that can be adjusted, if needed, via the controller's telemetry interface.

If the ventricular rate falls below a pre-set minimum (50-80 beats per minute), a pacemaker 39 (FIG. 11) may be used to trigger the timing cycle and restore heart rate. In the event the pacemaker becomes ineffective, the linear motor controller 50 may incorporate a telemetry programmable lower limit for the cycle rate of the piston-valve to ensure that adequate blood flow is maintained. This feature may also provide vital circulation in the event of total cardiac arrest. Accelerated heart rates such as premature ventricular contractions (PVC) and tachycardia may also occur. An implantable pacemaker alone does not have the ability to correct heart rates that are too rapid. However, the linear motor controller 50 may optionally incorporate features similar to currently available implantable cardioverter/ defibrillators to restore normal cardiac rhythm. If this should prove unsuccessful in reducing heart rate, the controller 50 may be adjusted to alter the motion of the piston-valve to minimize the damage to the blood cells due to high velocity flow through the piston-valve. This alteration in motion may consist of slowing down or stopping the piston-valve momentarily on its return stroke if a PVC or any type of tachycardia is detected. If extended tachycardia is detected, the piston-valve cycle rate may be adjusted to synchronize with every other or every third, etc., heart beat as well as adjusted to slow down or stop on the return stroke as necessary to minimize high velocity blood flow during ventricular ejection.

Figure 9A:
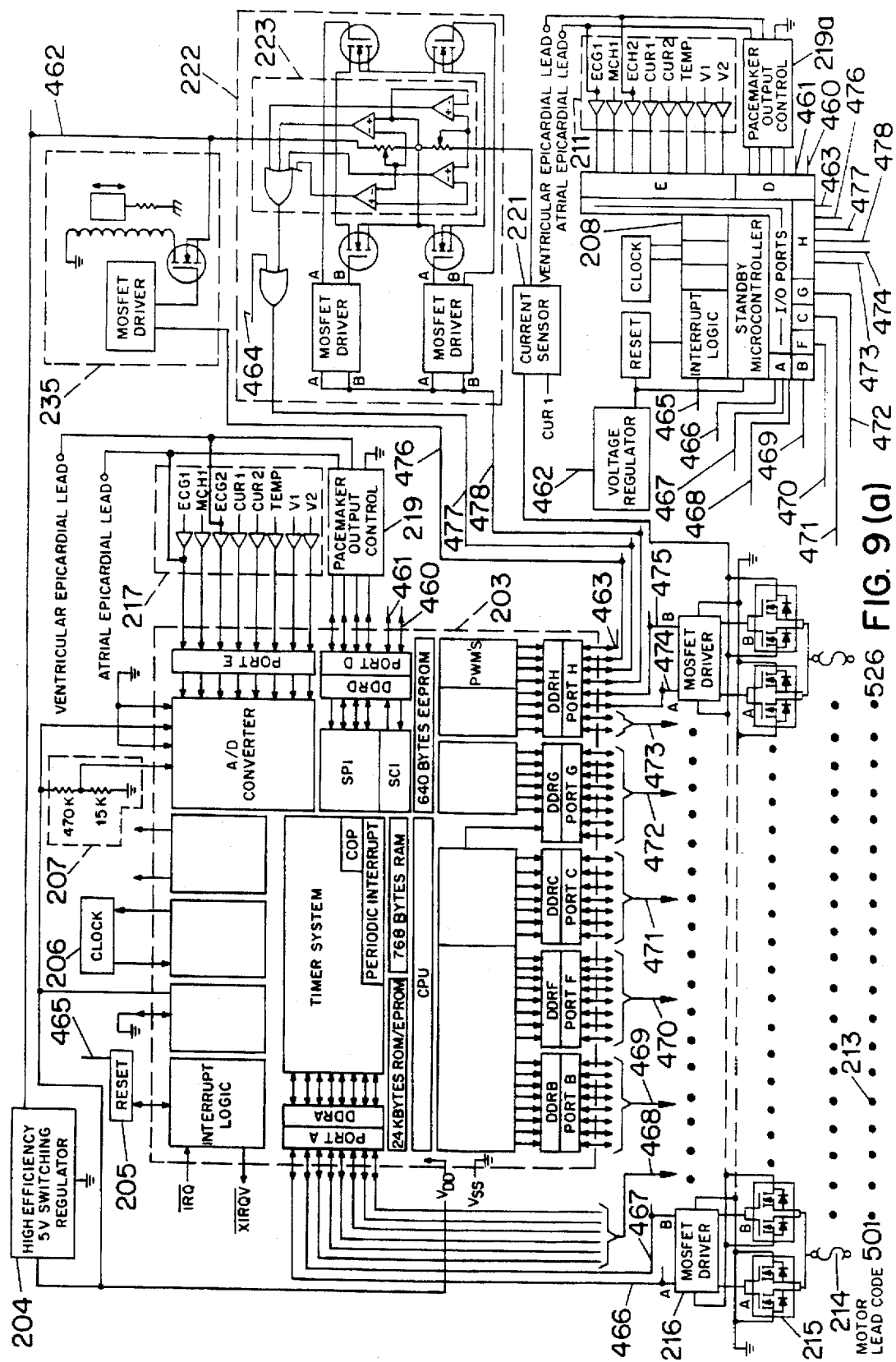
FIGS. 9(a)–9(c) are schematic circuit diagrams of a controller circuit in accordance with the invention.
Figure 9B:
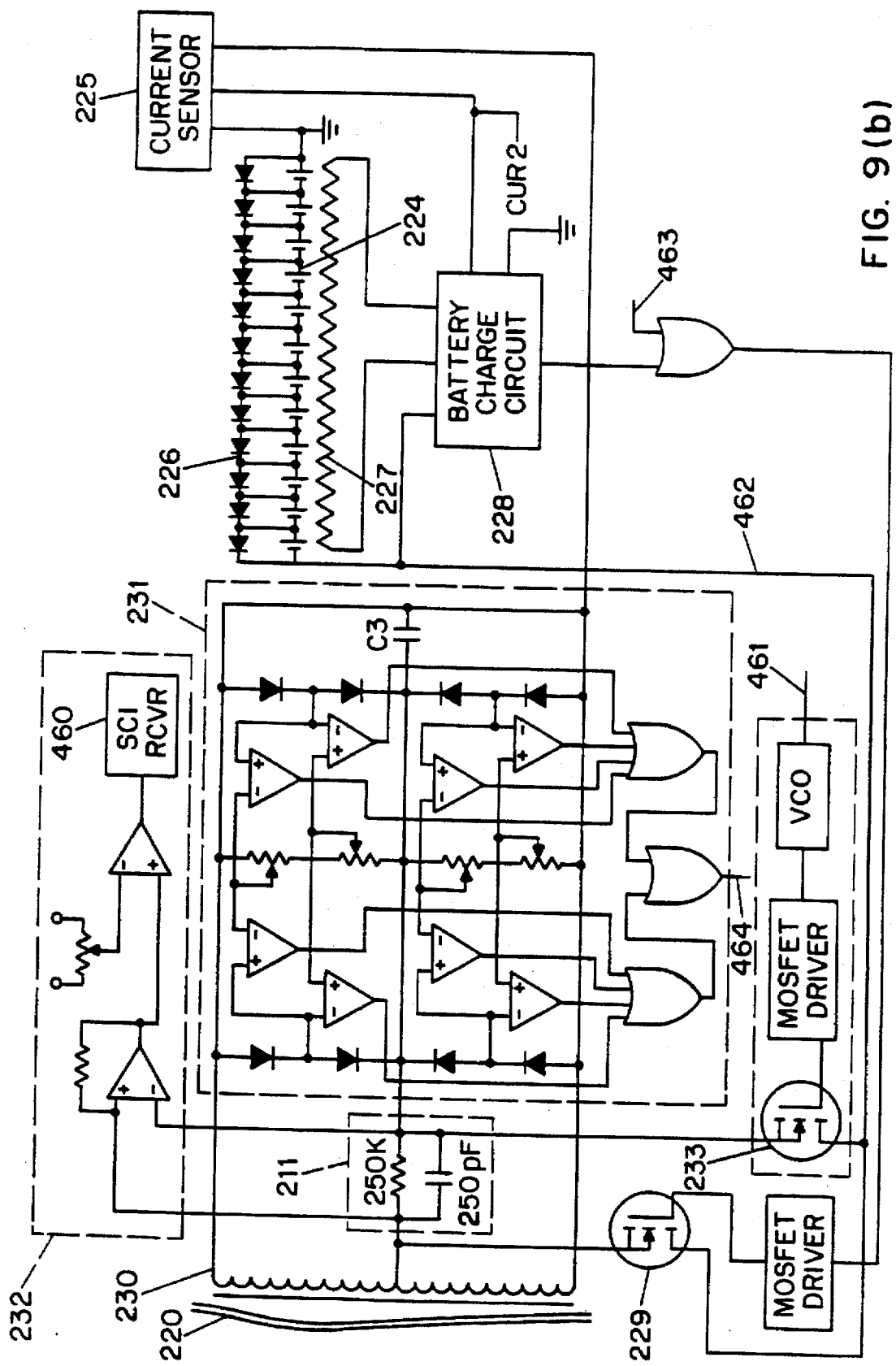
Figure 9C:
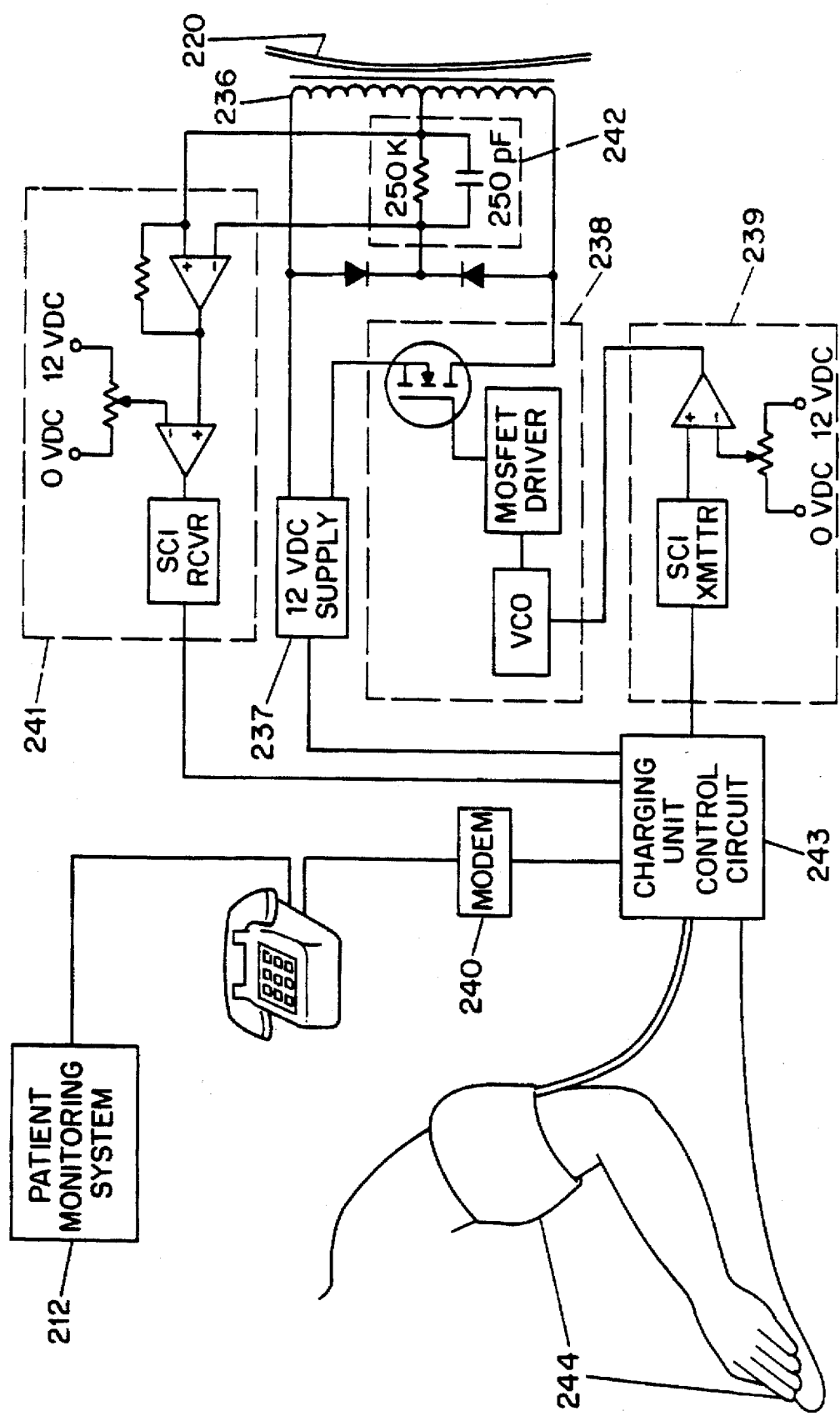

FIGS. 9(a), 9(b) and 9(c) are schematic circuit diagrams of a controller circuit used to generate the lead outputs required, as shown in FIGS. 7(a)-7(j) and FIG. 8 as well as the failure mode correction, and fault indication previously discussed and the telemetry discussed hereinafter. The microcontroller 203 shown in FIG. 9(a) is used as the main logic unit. Many other types of programmable logic devices could be used in this application in place of the microcontroller 203, such as a programmable logic controller (PLC) or gate array (PGA) or even an application specific integrated circuit (ASIC). These could be arranged to perform the required control algorithms for the linear motor.

However, the microcontroller products currently available provide a relatively complete set of the features required for a controller for an implantable circulatory assist device using the linear motor drive described in FIGS. 1, 7 and 8. The components of the microcontroller 203 include:

- A Central Processing Unit (CPU)—A coded binary instruction based logic unit similar to that used in microprocessors, programmable using machine language, assembler and high level compiled code such as that designated "C".
- A Read Only Memory (ROM), Electrically Programmable ROM (EPROM), and Erasable EPROM (EEPROM)—Memory spaces for program instructions, data and default values for variables.
- A Random Access Memory (RAM)—Memory space for variables used by the program.
- Input/Output (I/O) Ports A–H—Connections through which digital or analog data may be transferred to or from the microcontroller. These ports are used to control the switching sequence of the power semiconductors that control electrical current to the motor windings, send and receive serial data that can be used to adjust program variables within the microcontroller or send out information identifying faults or other performance data, as well as various related tasks.
- An Analog and Digital (A/D) Converter—A portion of the microcontroller that converts analog signals acquired via the I/O ports, such as total current to the motor, to digital information that can be used by the CPU.
- Pulse Width Modulators (PWM's)—Special output ports which can be programmed to rapidly switch on and off power semiconductors or other devices for programmable durations (pulse widths) that can vary in response to some feedback signal or other control. PWM's are useful in motor controls for current limiting algorithms as discussed above.
- A Serial Communication Interface (SCI) and a Serial Peripheral Interface (SPI)—These interfaces transmit or receive serial information via the I/O ports. This serial information can be a digital representation of any of the analog signals being processed by the A/D converter being transmitted out to be interpreted for diagnostic purposes, or incoming data providing instructions to adjust variables in the linear motor control algorithm.
- A Computer Operating Properly Watchdog Timer (COP) —This timer counts to a specified value and then resets the microcontroller to the beginning of the program currently being run, or one being pointed to by a reset vector, unless the program currently being run continually resets the timer to zero before it reaches the specified value. This serves to "free-up" a controller that has "locked-up" due to a corruption of program instructions due to a voltage transient or other outside influence.
- The microcontroller 203 is provided with power from a regulated 5 volt voltage source. However, to minimize power consumption and heat generation, a 3 volt unit may be used, powered by a high efficiency 3 volt switching regulator. A reset circuit 205 with low voltage protection to avoid memory corruption is also used. The microcontroller shown includes a crystal or other timing reference 206 to drive the main clock. A voltage divider 207 provides a regulated voltage reference for the microcontroller's built-in analog-to-digital converter. A standby microcontroller 208 is included, which can automatically isolate power to the primary microcontroller 203 if more than a predetermined number of computer operating properly watchdog timer (COP) resets are detected on the primary microcontroller within a predetermined interval or it can be manually activated via a telemetry interface connected to the SCI on each microcontroller. The back-up microcontroller 208 operates in "stop-mode" until activated to ensure minimum power consumption. It requires a voltage regulator, reset circuit, reference crystal, and voltage reference, similar to the primary microcontroller 203.

The microcontroller I/O ports A through H are used to drive a power semiconductor array 213, which controls current flow through the motor windings. Each motor lead is provided with a thermal circuit breaker or other passive over-current protection device 214, a complementary pair of power transistors 215 which permits current flow in either direction through each motor lead, and associated driver electronics 216, required for operation of the power transistors 215 by the logic level outputs from the microcontroller. The array of power transistors 215 may optionally be configured to passively or actively permit current flow in the reverse direction from the applied potential, on selected or all leads, thereby permitting the linear motor to be regenerative (i.e., if the load on the piston reverses such that an applied force is assisting movement rather than opposing movement, the controller can use the assisting force to return energy to the rechargeable battery cells, thereby reducing power consumption). This may be useful near the end of the piston travel where piston momentum will tend to drive the piston forward while the motor is trying to slow it down. The stored kinetic energy in the piston can be partially recovered using regeneration.

Each microcontroller 203 and 208 is provided with independent signal conditioning and isolation arrangements 217 and 218 for all incoming analog signals. These analog signals comprise (1) an (amplified) ECG signal output from a separate implanted pacemaker (ECG1) which may be used as a synchronizing signal for reciprocation of the pump module in implantable applications (see FIG. 11), (2) an (amplified) marker channel signal output from a separate implanted pacemaker (MCH1) which may be used as an alternate synchronizing signal if ECG1 is not available (A marker channel output from a pacemaker is a logic signal that indicates when the pacemaker control logic has detected a particular electrocardiological event such as a P wave, a QRS wave, or when the pacemaker has transmitted its own electrical stimulus to the heart.), (3) an ECG signal acquired from the epicardial lead (ECG2), which can be used as a synchronizing signal, (4) a voltage signal from the current sensor or other device indicating total current to the motor windings (CUR1) which may be used in conjunction with a PWM algorithm to efficiently limit motor current, (5) a voltage signal from the current sensor or other device indicating total current delivered to the internal rechargeable battery by the charging circuit (CUR2), which can be used to control charging rate efficiently using a PWM algorithm, (6) a voltage signal indicating battery temperature (TEMP) generated by the voltage drop across a thermistor or other temperature indicating means which can be used to detect an overcharge condition in the internal rechargeable battery, (7) a voltage signal indicating total voltage output from the internal rechargeable battery (V1), which can be used to detect an overcharge condition or detect that one or more of the cells has reversed, and (8) a voltage signal sensed across all or a selected group of motor windings (V2), which can be used to detect movement of the piston caused by flow of fluid.

Because all of the windings shown in FIGS. 7(a)-7(j) are connected in series to each other, any movement of the piston will generate an emf that can be detected from motor leads on either side of the piston. The signal (V2) may thus be used to detect ejection by the recipient's native ventricle (s) in VAD applications or native atria in TAH applications so that the motor may be synchronized when all ECG and marker channel signals (ECG1, ECG2 and MCH1) are lost. If no signals are detected from analog inputs ECG1, ECG2, MCH1 or V2, the controller will default to a fixed cycle rate of the piston back and forth through the hollow cylinder based on a value programmed in the microcontroller. The microcontroller includes programming to sense when the motor current indicated by CUR1 increases or decreases during a given piston stroke relative to previous strokes and will delay or advance subsequent strokes to minimize the current being drawn by the motor. The changes in current drawn by the motor in VAD applications could be caused by residual functioning of the recipient's native heart. For example, if the piston is returning down the cylinder toward the proximal end with the pump implanted as a VAD in a ventricular outflow vessel and the ventricle ejects, the current drawn by the motor will increase due to the flow of blood moving in the opposite direction that the piston is moving.

By programming the controller to seek out the cycle rate of the piston that results in minimum current being drawn by the motor, the piston reciprocation can be indirectly synchronized with any residual cardiac function still present to the maximum extent possible. However, any adjustments made by the controller to the piston cycle rate in this mode of operation would not preclude the programmed minimum number of piston strokes per minute from being completed to maintain minimum circulatory system flow requirements. The reference ground for these analog inputs, as well as the reference ground for the microcontroller analog-to-digital converters, may be connected to an electrically conductive surface on the outside of the controller 50 so that charge equilibrium with the recipient's body is maintained.

Two analog outputs provided from pacemaker units 219 and 219(a) connected to each microcontroller in FIG. 9(a) may also be incorporated for providing single or dual chamber pacing. The output threshold voltage for these signals may be programmable via the telemetry interface discussed in more detail later.

Current to the motor windings is measured using a Hall effect current sensor 221 or other efficient current sensing means. This current signal is used by the active microcontroller 203 or 208 to PWM current to the motor using a power transistor bridge 222. The PWM current limiting algorithm in the microcontroller consists of a program segment that compares the current level indicated at analog input CUR1 to programmable upper and lower limits for current to the motor. As long as CUR1 is below the upper limit, no PWM current limiting will be active. Once the upper limit is exceeded, the PWM algorithm will shut off the power semiconductors in the bridge 222 until current drops below the lower limit, at which time, the power semiconductors in the bridge 222 will be turned back on. This will continue until CUR1 stops exceeding the upper limit for current.

The transistor bridge arrangement 222 is configured to provide one or more redundant back-ups for each power transistor. Comparators and logic gates 223 are incorporated to provide a logical fault indication back to the active microcontroller if one of the power transistors in the bridge has failed. In the configuration shown, two power transistors in series are placed in parallel with two other power transistors in series. A failure of any single power transistor will not cause the overall state of the bridge to be incorrect. The fault detection circuit relies on the fact that the potential at the midpoint between each pair of series power transistors should stay approximately half-way between the upper and lower rails of the bridge. A window comparator is used to detect when this potential deviates from the expected midpoint potential by more than an acceptable range. The motor current PWM algorithm is only expected to be active during lightly loaded conditions such as the piston return stroke or holding modes. During the piston drive stroke, it is expected that back emf generated by the motor will be sufficient to limit current through the windings without the use of PWM.

An internal rechargeable battery 224 shown in FIG. 9(b) consists of a number of high energy density secondary cells, such as nickel-metal-hydride. Charging current to these cells is indicated by a Hall effect current sensor 225 or other high efficiency current sensing device. The internal battery may also incorporate passive bypass diodes 226 which prevent the voltage drop and associated power loss resulting from a cell reversal from approaching an unacceptable level. The battery assembly may also incorporate one or more thermistors 227 or other temperature sensing devices which provide an indication of cell temperature to the active microcontroller for the purpose of terminating charging at a safe condition. This cell temperature indication may also be sensed by an optional independent battery charging supervisory circuit 228. This independent circuit may provide stand alone supervision of internal battery charging, thereby reducing demand on the active microcontroller, or simply act as a redundant back-up to provide additional protection from overcharging. In the latter configuration, the active microcontroller 203 or 208 and the independent charging supervisory circuit 228 can act through an OR gate to PWM or isolate current from the internal battery using a power transistor 229.

Power for the internal battery charging circuit is obtained via a subcutaneous secondary coil 230. This coil is connected to a capacitor/rectifier circuit 231 that is tuned to the carrier frequency being transmitted trancutaneously to the secondary coil 230. The rectifier may incorporate redundant diodes and a fault detection circuit as shown, which operates similar to the power transistor bridge 222 and logic circuit 223 of FIG. 9(a), except that the power transistors are replaced by diodes. This tuned capacitor/rectifier circuit may also incorporate a filter arrangement 211 to support serial communication interface (SCI) reception via the secondary coil 230. A level detection comparator 232 is provided to convert the analog signal produced by the filter 211 into a digital signal compatible with an SCI receiver 460. A power transistor 233 or other modulation device may also be incorporated to support SCI transmission via the secondary coil 230. A redundant transistor bridge such as the bridge 222 used for PWM current limiting may be used in place of the transistor 233 for improved fault tolerance. This SCI interface provides for changing programmable settings used by the control algorithm and monitoring of analog inputs to the microcontroller such as ECG1, ECG2, MCH1, CUR1, CUR2, TEMP, V1, and V2.

A pager 235 shown in FIG. 9(a), consisting of a small mass oscillated at low frequency by a solenoid or other device to produce a vibrating sensation suitable for alerting the recipient to a fault condition, is mounted within the controller 50. Alternatively, the pager may be a small speaker producing an audible tone through the patient's skin. The pager is driven by a PWM output from the active microcontroller through a suitable amplifier. The pager may be activated for short periods, separated by decreasing intervals, as internal battery power approaches depletion. The pager will be activated continuously when an internal fault other than low battery charge is detected. The fault may be identified via the telemetry interface on the controller to assist in determination of corrective actions. The continuous page may also be halted via the telemetry interface once the appropriate personnel have been informed of the fault.

The carrier wave received by the internal secondary coil 230 (FIG. 9(b)), is generated by an external primary coil 236 shown in FIG. 9(c) which transmits electromagnetic energy across the recipient's skin 220. The carrier frequency is generated by a DC power source 237 being modulated by a high frequency oscillator 238, or other suitable high frequency carrier generator. The carrier frequency may be further modulated by an external SCI transmitter circuit 239 to support telemetry as discussed earlier. A modem 240 may also be incorporated to support remote telemetry control and monitoring. The modem 240 is connected to an SCI reception circuit 241 which accepts a filtered output from a rectifier/filter circuit 242 similar to the filter 211 and receiver 232 shown in FIG. 9(b). A central charging unit control circuit 243 may also be required to manage charging and telemetry functions. The charging unit control circuit also incorporates an automatic sphygmomanometer and a non-intrusive blood oxygen level detector 244 or other arrangement to permit the recipient to determine his/her own blood pressure, pulse and/or blood oxygen level to facilitate remote patient monitoring and management.

A patient monitoring system 212 is also provided. This system consists of a combination of remote computer monitoring equipment and associated personnel, if necessary, that monitors the patient and implantable circulatory assist device status based on signals received through the transmission lines. Any of the analog input signals sensed by the microcontroller (ECG1, ECG2, MCH1, CUR1, CUR2, TEMP, V1 or V2) as well as patient blood pressure, blood oxygen level or any other physiological parameter that can be measured by the charging unit, can be monitored by the patient monitoring system. Any adverse trends or indications can be detected and reported to the patient, the patient's physician or an emergency care facility close to the patient, so that corrective action can be taken.

For implantable VAD applications, an optional internal rate-responsive dual chamber pacemaker algorithm can be incorporated into the controller 50 which becomes activated upon loss of the separate endocardial lead pacemaker ECG signal. Alternatively, all pacemaker activity can be performed by the controller. In this case, a pacemaker controller algorithm provides dual chamber pacing via the epicardial leads at an interval programmed to be slightly longer than the separate endocardial lead pacemaker interval. In addition, the controller pacemaker interval may be adjusted so as to increase or decrease heart rate in response to root mean square (RMS) input from a pressure transducer on the outside of the controller enclosure which measures the amplitude of intra-anatomic pressure waves or some other indication of the patient's level of physical activity. Pacing stimulus from the controller pacemaker inhibited if a normal ECG interval is sensed.

Upon loss of all ECG input signals in an implantable VAD application, the controller 50 uses signals sensed from the linear motor windings as a result of the slight movement of the piston-valve due to ejection of the left ventricle, to synchronize the piston-valve. If the detected heart rate falls below a programmable lower limit (e.g., 50–80 beats per minute), the controller 50 maintains reciprocation of the piston-valve at the preprogrammed lower rate limit. In this mode of operation, the controller monitors total current to the linear motor thereby detecting improper synchronization. This capability exists because the motor will draw more current than normal if the patient's native heart is not ejecting when the piston-valve is in its pumping stroke or when the patient's native heart is ejecting when the piston-valve is on its return stroke. Upon detection of improper synchronization, the controller makes the necessary corrections while maintaining the preprogrammed minimum stroke rate.

The controller 50 may further include diagnostic circuitry to interrogate the pump control circuitry and therapeutic control circuitry to deal with pump control during arrhythmias.

Figure 10A:
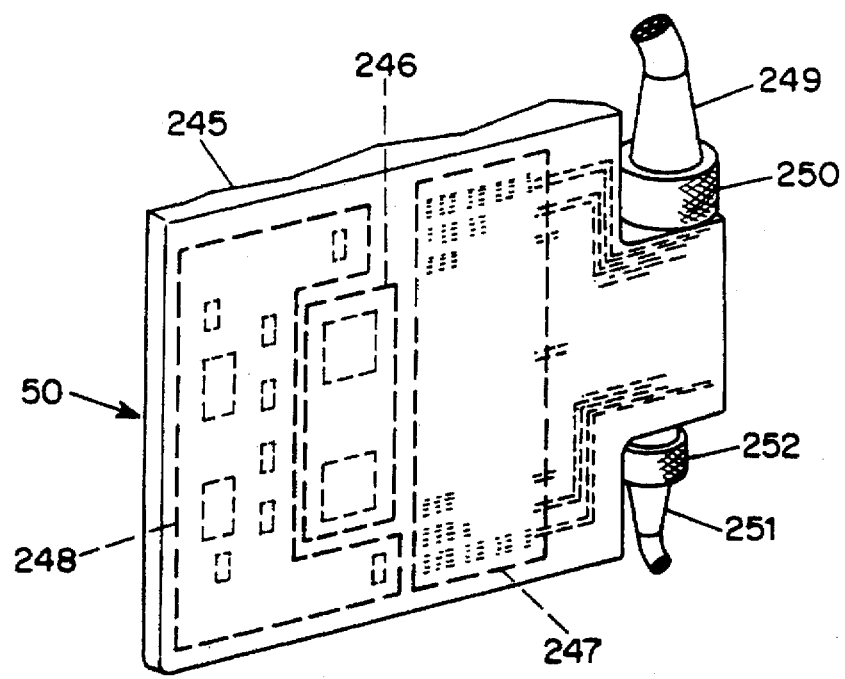
FIGS. 10(a) and 10(b) are perspective views showing the opposite sides of an implantable controller arrangement in accordance with the invention.
Figure 10B:
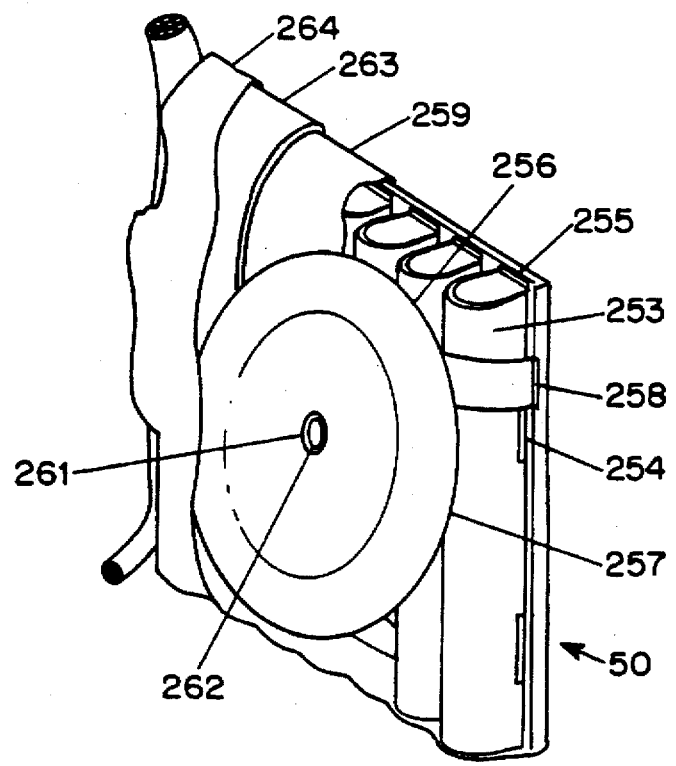

FIGS. 10(a) and 10(b) show a representative arrangement of an implantable controller 50. The inner face illustrated in FIG. 10(a) shows the arrangement of discrete circuit components enclosed in a housing 245, including two microcontrollers 246, a power transistor and driver array 247 and other conventional electronic circuit components 248. A main lead bundle 249 terminates as shown at a hermetically sealed cylindrical connector 250, which could be replaced with any other suitable connection arrangement. The primary ECG/marker channel lead bundle 251 from a separate pacemaker also terminates as shown at a hermetically sealed connector 252 or other suitable connecting arrangement. A series of rechargeable battery cells 253 are adhesively mounted to the outer surface of the printed circuit board as shown in FIG. 10(b). Passive bypass diodes 254, discussed above, may be mounted in the interstitial spaces between the battery cells to conserve space. The cell terminals have spot welded tabs 255 to facilitate mounting to the printed circuit board.

A disk 256 made from ferrite or other magnetically suitable material is used to improve electromagnetic coupling of the external primary charging coil 236 shown in FIG. 9(c) to an internal secondary charging coil 257. The secondary coil 257 and the disk 256 may be integral with the controller package as shown, or they may be an independently implanted component connected to the controller via a dedicated lead bundle. The integral charging coil 257 and disk 256 arrangement has tabs 258 to connect the secondary coil to the printed circuit board.

During assembly of the implantable controller, the rechargeable cells 253 may be covered with a protective shield 259, which is adhesively attached to the back of the disk 256 and to the back side of the circuit board. The shield, along with all other exposed circuit components, may then be coated with a hermetically sealed encapsulant 264, such as clear polyurethane. A sheath (not shown) of corrosion-resistant material such as titanium may optionally be bonded around the outside of the hermetic encapsulation. This sheath will leave the secondary coil 257 and ferrite disk 256 exposed to ensure good electromagnetic coupling. The protective shield, encapsulation and optional sheath may be assembled in an inert gas environment so that a volume of inert gas is trapped within the shield 259. This will provide a void space filled with inert gas such as nitrogen, into which the rechargeable cells may vent evolved gas if an overcharge condition occurs. If the evolved gas released is sufficient to pressurize the void space formed by the shield 256 above a safe level, a relief feature 258 in the shield will rupture, releasing the gas mixture into the space surrounding the controller assembly through a hole 261. A dacron velour or other suitable material may be used to form a protective sack 262 into which the released gas mixture may collect. If the gas released inflates the sack partially, the external charging coil will be mechanically decoupled from the internal charging winding, thereby preventing further generation of evolved gases due to overcharging. The gas may be extracted when the controller is replaced if it has not already permeated out through the sack and the patient's skin.

For implantable TAH applications, the controller 50 can optionally incorporate a rate responsive algorithm which uses RMS input from a pressure transducer on the outside of the controller enclosure. The RMS input measures the amplitude of intra-anatomical pressure waves or some other indication of the patient's level of physical activity. This algorithm may provide for a programmable lower heart rate limit (e.g., 50–80 beats per minute) and upper heart rate limit (e.g., 110–140 beats per minute) between which the controller may adjust the TAH rate in response to the patient's level of physical activity. The TAH may optionally incorporate intra-aortic and intra-pulmonary pressure transducers which provide feedback to the controller used to regulate the patient's systolic and diastolic pressures between preprogrammed limits in response to the patient's level of physical activity. Four pressure transducers at each location permit the use of 2 out of 3 logic to identify signal faults. An additional transducer may be installed as a spare to be used in the event a fault is detected. The TAH controller monitors total current to the linear motor for detection of indications that venous collapse has occurred due to excessively low inlet pressure. Upon detection of venous collapse, the controller slows or reverses direction of the piston-valve to correct this condition. In addition, the speed of the piston-valve can be subsequently decreased by the controller to avoid recurrence of this condition.

Temporarily implanted and extracorporeal devices may optionally incorporate manually controlled settings for stroke interval or some provisions for automatic synchronization with the patient's native heart as discussed above for the implantable devices.

The separate endocardial lead pacemaker used in VAD applications can be similar in every way to a conventional rate responsive dual chamber (DDDR) type currently available for implantation except that it comprises an additional connection for an external ECG/marker channel output. The currently used DDDR pacemakers provide ECG and marker channel signals as outputs available via their telemetry interface. The additional connection requires that the ECG and marker channel signals be routed continuously to the receptacle where the endocardial leads will be connected. The ECG and marker channel signals from the separate endocardial lead pacemaker are preferably amplified to provide a peak signal strength of approximately 100 mV to preclude interference from environmental sources. The ECG and marker channel leads can be routed subcutaneously from the hermetically sealed connector at the separate endocardial lead pacemaker to a hermetically sealed connector on the enclosure of the controller. The ECG and marker channel lead bundle can comprise a four conductor shielded cable similar to that described for the main lead bundle.

A failure of both the main and back-up microcontrollers that drive the linear motor controller, a loss of power to the controller circuit or a mechanical failure in the pumping mechanism, (e.g., a jammed piston-valve) may result in loss of circulatory assist in VAD applications or loss of circulation all together in TAH applications. In VAD applications, residual function of the patient's native heart will provide some circulation. The VAD arrangements described have been analyzed by computational fluid dynamics in the failed condition where the patient's native heart continues to eject blood through a stationary piston-valve. Reynolds shear stress in the bulk blood flow is within acceptable limits and no perpetual stagnation areas are indicated. However, if the piston-valve actually becomes jammed in the cylinder, which should be precluded by the materials used, the sliding clearances and the geometric tolerances specified for the piston-valve and cylinder, there is a risk that blood flow to the coronary arteries of the patient's native heart may be restricted during diastole caused by closure of the check valve in the piston-valve.

If the failure is related to a failure of the linear motor microcontroller or loss of power to the controller, ejection from the patient's native heart and the small gradient across the open piston-valve should be sufficient to displace the piston-valve toward the discharge end of the cylinder. This displacement will permit normal filling of the patient's coronary arteries during diastole as the piston-valve slides back down toward the inlet end because of the pressure gradient across the closed valve. The self-synchronizing feature of the linear motor/ controller will permit the VAD to be restarted once the power to the controller is restored or the controller is replaced. Administration of drugs to the patient which lyse clots or prevent clot formation altogether may be necessary prior to restarting the VAD. In TAH applications, it is generally accepted that a loss of power will cause a total loss of cardiac output. Therefore, in TAH applications, the power source to the linear motor controller must provide completely uninterruptable service. Accordingly, the controller for the linear motor preferably incorporates a redundant microcontroller which monitors performance and takes control when a fault in the primary microcontroller is detected.

As discussed above, transcutaneously coupled primary and secondary coils are used to transmit energy from a source outside the patient's body to the charging circuit for the internal rechargeable cells. For implanted VAD applications, it is expected that a charging period will be required at regular intervals. For implanted TAH applications, where no back-up ventricular function is available, it is expected that the patient will wear an external charging unit most of the time to prevent loss of power to the TAH controller. This external charging unit may be portable, such as a vest containing numerous rechargeable cells with a total capacity sufficient to operate the TAH for several days, or a fixed unit that operates on household electrical service. The internal rechargeable cells for implantable TAH applications will "float" on charge until the patient must remove the external charging unit (e.g., to shower or change external charging units).

The internal charging circuit will provide protection against overcharging by isolating charging current to the internal batteries when an overcharge condition is detected. Overcharge may be detected by decrease in current flow, increase in cell voltage or increase in cell temperature. Since the rechargeable cells may vent evolved gases if all overcharge detection measures fail to initiate overcharge current isolation, another back-up mechanism is available in the form of a passage surrounding the battery vents. This passage may comprise a protective seal which will rupture before the maximum safe internal pressure is reached as discussed above.

A surgically implantable pump in accordance with the invention may be implanted directly into an aorta or pulmonary artery, which can be called ventricular outflow arteries since they receive blood directly from the ventricular chambers of a heart. This method does not involve trans-valve placement of the pump. Instead, it relates to implanting a pump downstream of an aortic or pulmonary valve, leaving the valve intact and unimpeded and allowing valve activity to continue normally while the pump is operating. In one preferred method of implantation, an aorta or pulmonary artery is transected, i.e., cut in a manner which crosses the main axis of the artery, downstream of the aortic or pulmonary valve. A segment of the artery can be excised to facilitate pump implantation. The two exposed ends of the transected arterial wall are attached around the entire periphery of the pump inlet and outlet, by a connecting arrangement such as suturing the arterial ends to the previously described vascular attachment devices. Thereafter, all blood pumped out of the ventricle and through the aortic or pulmonary valve passes through the pump, with the minor exception of blood which immediately leaves the aorta and travels through the coronary arteries. The pump imparts additional pumping force to the ejected blood, to augment, or in some situations entirely replace, the pumping activity of the damaged or diseased ventricle. The pump augments any residual function in damaged and diseased hearts, and it can optimize the contribution of an otherwise inadequate heart to total output. In some cases, it can allow the heart to regain strength over time, by giving the heart a chance to empty completely and exercise under conditions which are not too demanding. Just as proper exercise can increase the strength and stamina of other types of muscle, it can help a heart which has been damaged by a heart attack or other trauma to regain strength, so that the natural heart function will be able to carry a greater portion of the load as days, weeks and months go by.

Figure 11:
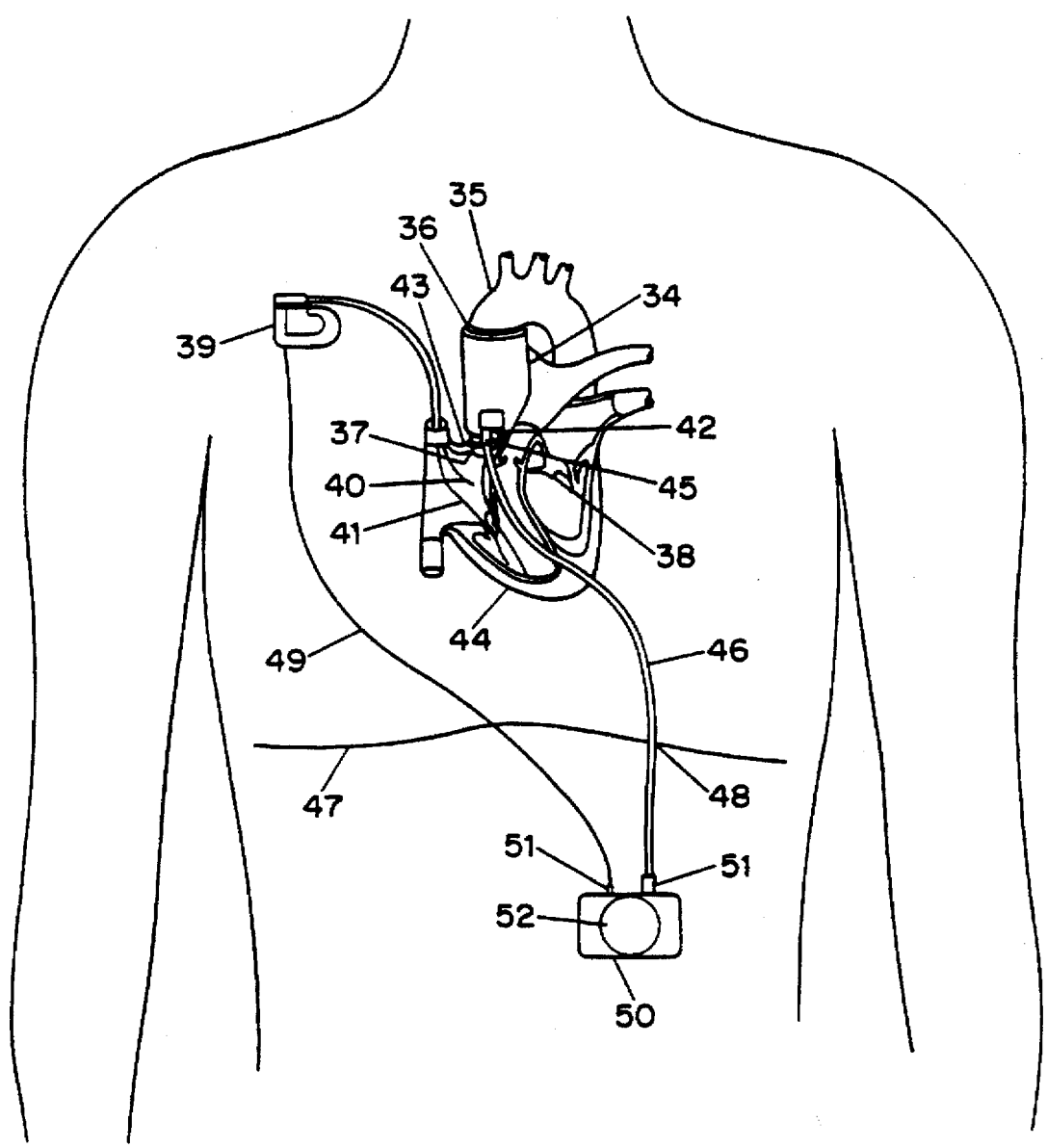
FIG. 11 is a schematic illustration showing the anatomical arrangement of a surgically implantable pump with a reciprocating piston-valve in accordance with the invention implanted as a left ventricular assist device.

FIG. 11 illustrates an anatomical arrangement of the LVAD depicted in FIG. 1 implanted in a patient. The LVAD 34 may be attached at its discharge to the patient's remaining distal ascending aorta 35 via a sewing cuff 36 as discussed earlier. The inlet end of the LVAD may be attached to the patient's proximal ascending aorta via another sewing cuff 37 immediately downstream of the inlet to the patient's coronary arteries (not shown) and aortic valve 38.

In the illustrated configuration, a separate conventional style dual chamber pacemaker 39 is located the patient's pectoral region with endocardial leads 40 and 41 entering the patient's superior vena cava and routed into the right atrium and right ventricle. Epicardial leads 43 and 44 are optionally provided with the LVAD and are routed to a hermetically sealed molded strain relief 42 adjacent to the strain relief 45 for the main lead bundle 46. The main lead bundle 46 for the LVAD can penetrate the patient's diaphragm 47 through a small incision 48 that is surgically reinforced after the cable is routed through or may alternatively be routed between the xiphoid process of the sternum and sternal diaphragm, thereby avoiding any penetration in the recipient's abdomen.

The pacemaker 39 can be a conventional type as discussed earlier, but with a slight modification to incorporate a connection through which continuous amplified ECG/marker channel signals are provided. These signals are carried by a small lead bundle 49 and terminate at the controller 50 using hermetically sealed connectors 51. The controller contains the microcontroller unit, power transistors, rechargeable batteries and other supporting circuitry that drives the LVAD's linear motor. The controller's rechargeable batteries are recharged via a transcutaneous energy transmission system (TETS) coil which is also used for telemetry functions as described above, housed within the controller enclosure 52.

Figure 12:
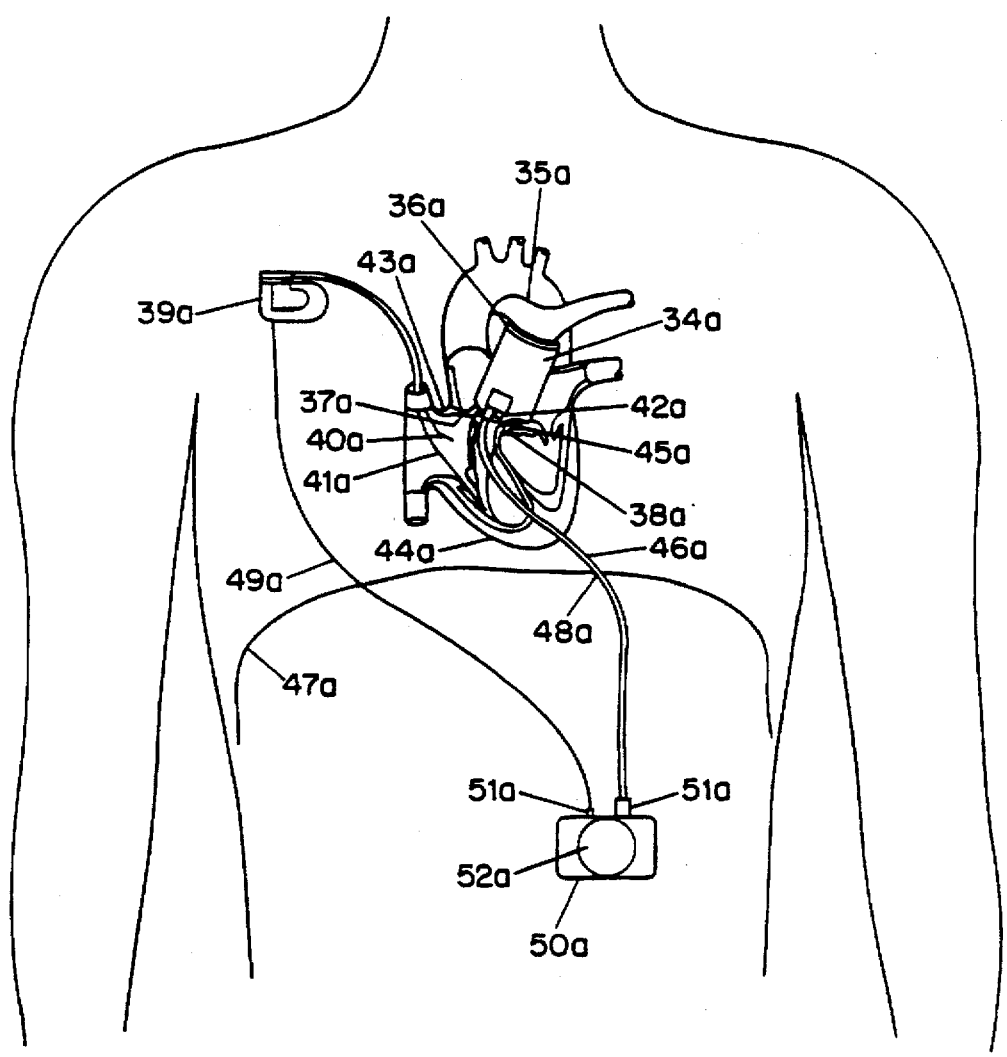
FIG. 12 is a schematic illustration showing the anatomical arrangement of a surgically implantable pump with a reciprocating piston-valve in accordance with the invention implanted as a simplex right ventricular assist device.

FIG. 12 illustrates an anatomical arrangement of a surgically implantable pump depicted in FIG. 1 implanted as a simplex right ventricular assist device (RVAD). In this arrangement, a reciprocating pump 34(a) is implanted in the main pulmonary artery leading away from the right ventricle in the same manner as the pump implanted in the aorta described above. Because of different anatomical constraints and physiological requirements, the size of the reciprocating pump 34(a) implanted as a RVAD may be somewhat smaller than when implanted as a LVAD. Optimal pump sizes for both LVAD and RVAD placement will be determined by physiological requirements, patient size, respective arterial size and individual support requirements.

Figure 13:
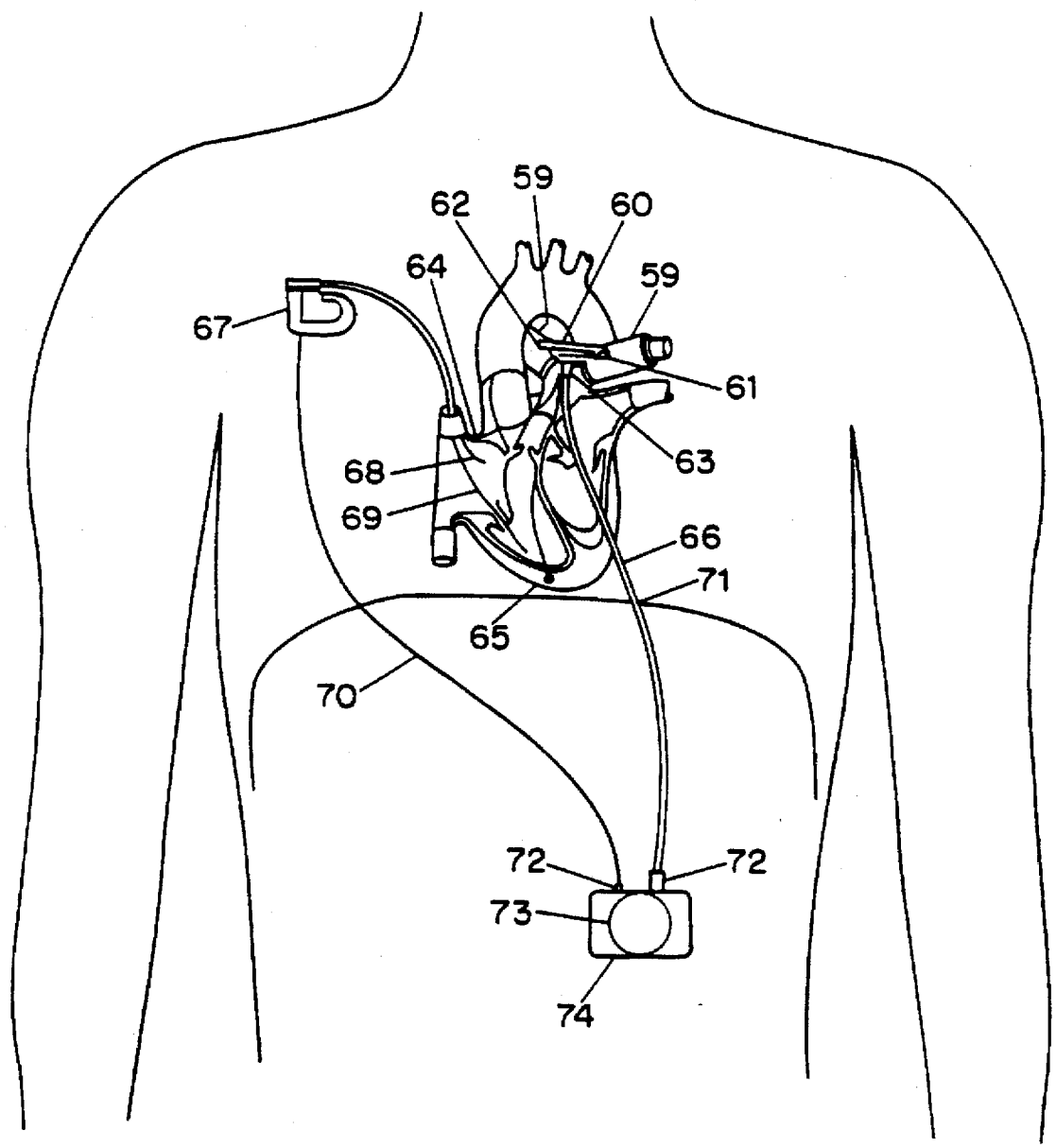
FIG. 13 is a schematic illustration showing the anatomical arrangement of a surgically implantable pump arrangement in accordance with the invention implanted as a duplex right ventricular assist device.

While a simplex RVAD is preferred, the symmetric right and left branches of the pulmonary artery lend themselves to a duplex arrangement as shown in FIG. 13. A duplex RVAD arrangement permits the cancellation of reaction forces and permits the use of two smaller pump modules versus one large pump module (for example, 20–40 cc fluid displacement per pump module for the duplex arrangement versus 40–80 cc displacement for a simplex arrangement) and may be compatible for combination left and right VAD (Biventrical assist device (BIVAD)) implantation.

In the duplex arrangement shown in FIG. 13, two pump modules 59 are implanted, one in each of the pulmonary arterial branches, with a strut 60 connecting the two modules. The reaction force created as the piston-valve within each pump module forces blood out its discharge is mostly cancelled through the connecting strut 60, since these forces will be approximately equal and opposite. This will minimize any unnatural sensations felt by the recipient.

The lead bundle for each pump module originates at corresponding sealed strain reliefs 61 and 62 and the bundles join at a common molded junction 63. Epicardial ECG leads 64 and 65, which originate at locations on the recipient's right ventricle and atria as shown, also enter a main lead bundle 66 at the common molded junction. Alternatively, they may enter the main lead bundle 66 at any other convenient location.

The duplex RVAD implantation may also incorporate a separate commercial pacemaker 67, which uses endocardial leads 68 and 69 to sense/stimulate atrial and ventricular activity. The separate pacemaker preferably provides an amplified ECG and marker channel output, as in the LVAD implantation depicted in FIG. 11, to a pump controller 74 via a subcutaneous lead bundle 70. The main lead bundle 66 penetrates the recipient's diaphragm 71 and terminates at a hermetically sealed cylindrical connector 72, along with the pacemaker ECG/marker channel lead bundle 70. A secondary coil 73 of the type discussed earlier for the LVAD implantation is provided in the pump module controller 74.

Figure 14:
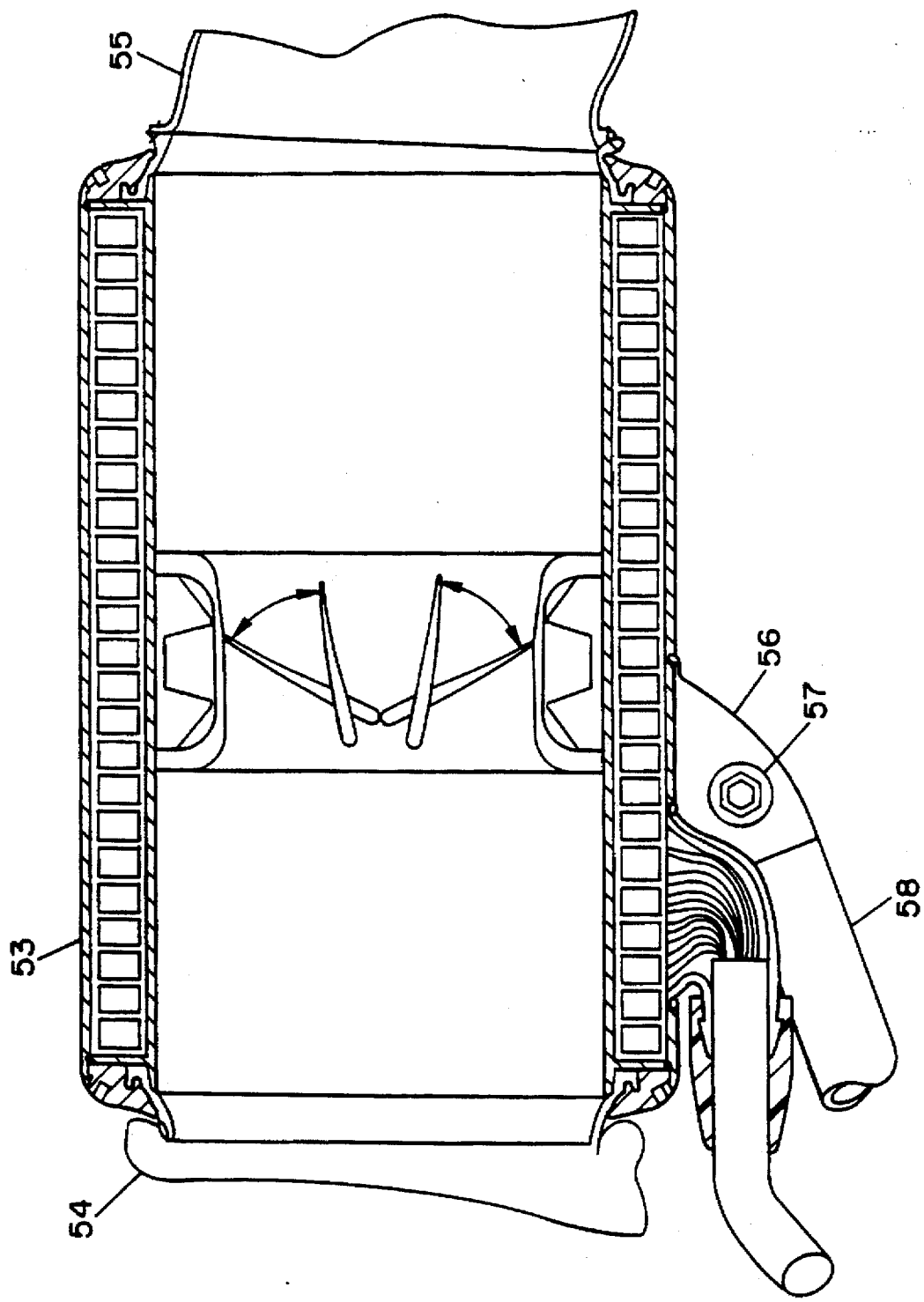
FIG. 14 is a longitudinal sectional view illustrating another embodiment of a surgically implantable pump arranged in accordance with the invention.

FIG. 14 shows a cross-section of linear motor driven pump 53 suitable for use in the configuration shown in FIG. 13, with vascular attachment cuffs sewn to pulmonary arterial vessels 54 and 55. This pump is similar to the pump of FIG. 1, except that the additional strut attachment 56 is provided. A self-locking fastener 57 or other securing device may be used to secure a strut 58 to the strut attachment. The strut 58 is provided to connect two reciprocating pumps installed in the duplex arrangement shown in FIG. 13 and is used to cancel reaction forces.

Figure 15:
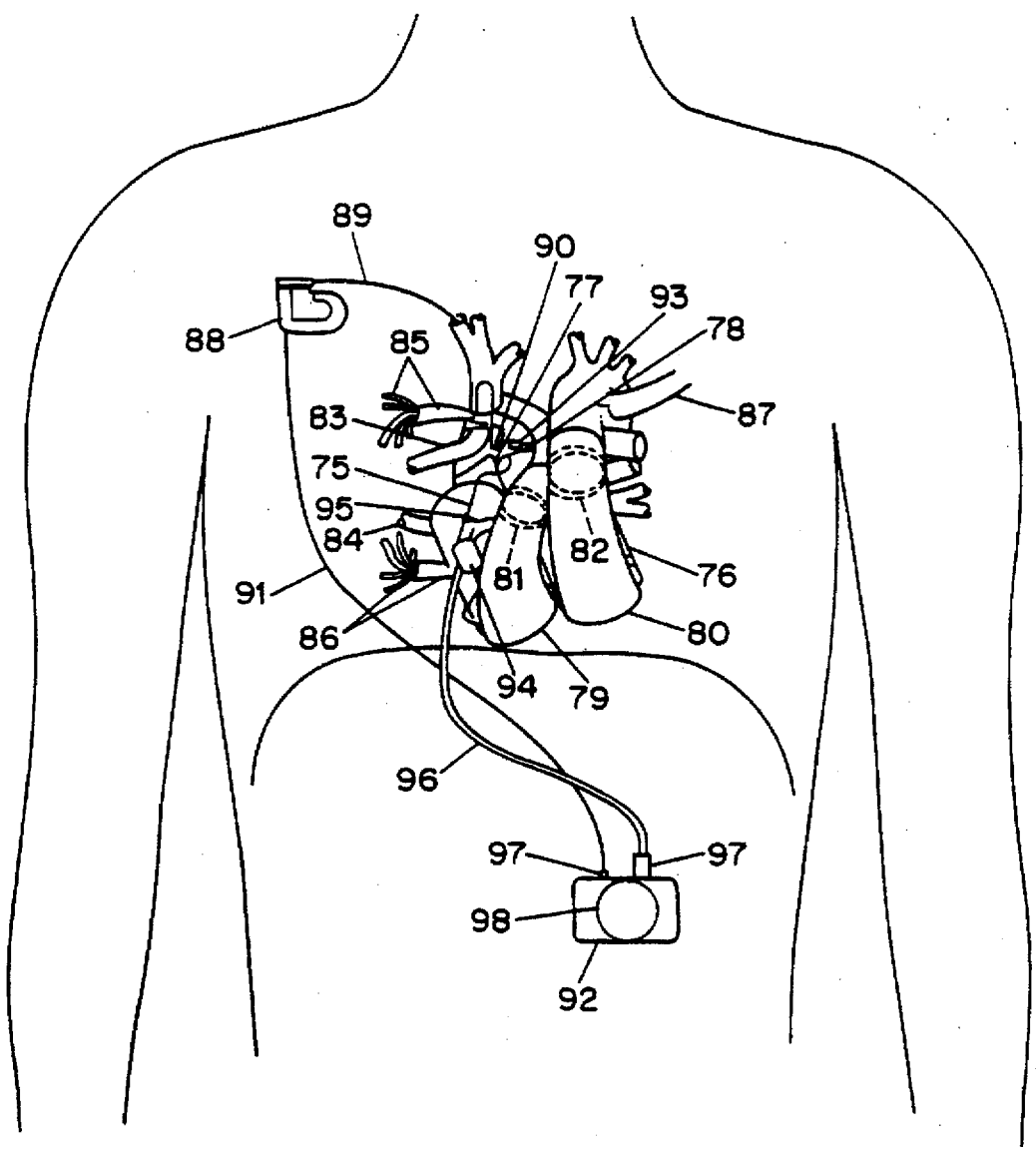
FIG. 15 is a schematic illustration showing the anatomical disposition of a surgically implantable pump arrangement in accordance with the invention in a duplex total artificial heart implantation.

FIG. 15 shows two pump modules 75 and 76 implanted in a duplex TAH configuration. The pump modules used in this application are similar to the pump shown in FIG. 1 or the pump shown in FIG. 14, but they may have a larger displacement (e.g., 70–100 cc) compared to previously discussed VAD pump modules, since the recipient's ventricles are completed removed.

The inlet ends of the pump modules 75 and 76 may be attached to the recipient's right and left atria, respectively, using sewing cuffs 77 and 78 respectively. The discharge end of the pump modules 75 and 76 are connected to the pulmonary artery and aorta, respectively, using vascular grafts 79 and 80, respectively. These grafts include conventional prosthetic heart valves 81 and 82, which can optionally be located nearer to the discharge of the pump modules. Alternatively, these valves can be positioned in the vascular grafts on the inlet side of the pump modules (i.e., tricuspid and mitral positions).

The duplex TAH implantation shown in FIG. 15 includes cardiopulmonary bypass cannulae 83 and 84 from the superior vena cava and inferior vena cava, respectively, held in place by clamps 85 and 86, respectively. These cannulae are routed to a standard cardiopulmonary bypass pump (not shown) which returns oxygenated blood to the recipient's aorta via a cannula 87 until the duplex TAH is fully implanted and activated, at which point the clamps 85, 86 and cannulae 83, 84 and 87 are removed and all vascular penetrations are closed. This bypass arrangement is similar to that used for all major cardiac operations and is compatible with all prosthetic implants discussed herein.

In the illustrated embodiment, a separate implantable pacemaker 88 is used to sense or pace the recipient's normal atrial activation and provide a marker channel signal which can synchronize pump reciprocation with atrial contraction. The pacemaker 88 can be a conventional single chamber type, sensing or stimulating right atrial contraction via an endocardial lead 89 which can be routed through the recipient's superior vena cava to a location near the recipient's sinus node 90, on the inner surface of the right atria. The ECG/marker channel signal generated by the pacemaker is carried by a subcutaneous lead bundle 91 to the controller 92. The signal can be amplified by the pacemaker internal circuitry to avoid electromagnetic interference, as discussed earlier.

An atrial ECG signal may also be acquired using an epicardial lead 93 as a primary lead which is routed to a hermetically sealed lead bundle penetration 94 on one of the two pump modules. The lead bundle penetration 94 also includes a main lead bundle 95 routed to the adjacent pump module and a main lead bundle 96 routed to the controller 92. The two pump modules 75 and 76 can be connected in parallel, i.e., with the lead bundle 95 being simply a continuation of the leads carried by the lead bundle 96 so that both pump modules can be operated simultaneously from the common controller 92. The main lead bundle 96 and the ECG/marker channel lead 91 terminate at hermetically sealed connectors 97 on the controller 92. The power cells within the controller are charged via a transcutaneous charging coil 98 as discussed earlier for the VAD applications. However, the external charging unit may operate most of the time for TAH applications, with the secondary cells within the implantable controller serving as an uninterruptable back-up power supply if the external charging circuit is broken. This may be required since no back-up arrangement to maintain circulation is provided by the duplex TAH implantation shown in FIG. 15 if power to the controller is lost.

Figure 16:
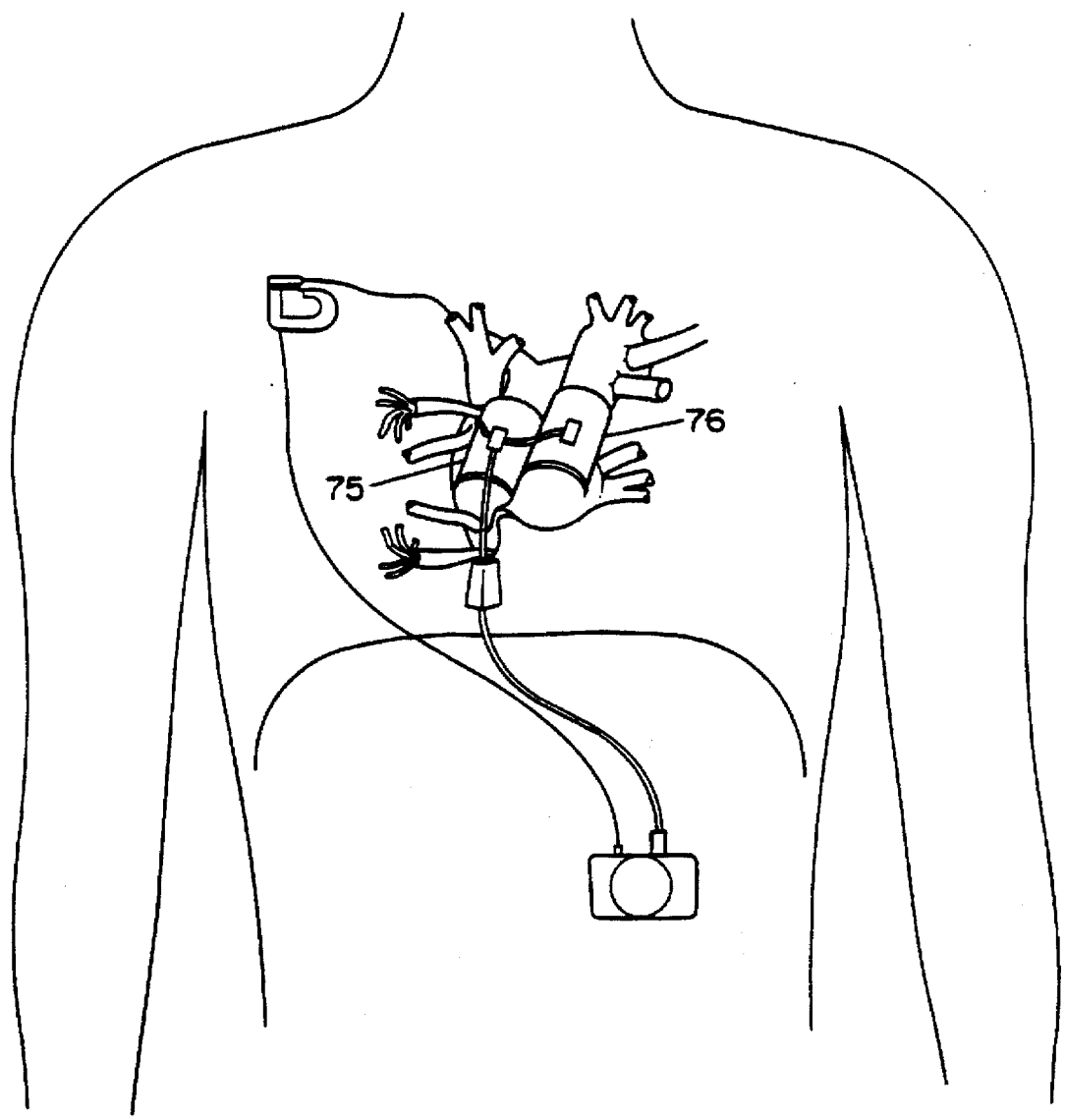
FIG. 16 is a representative alternate surgically implantable pump arrangement in accordance with the invention in a duplex total artificial heart implantation.

In an alternative embodiment shown in FIG. 16, the pump modules 75 and 76 are attached to the recipient's right and left atria in a more vertical arrangement. The sewing cuffs bend about an angle of approximately 90° and are made of a stiff material so as to avoid flexing inward under the weight of the pump modules.

Figure 17:
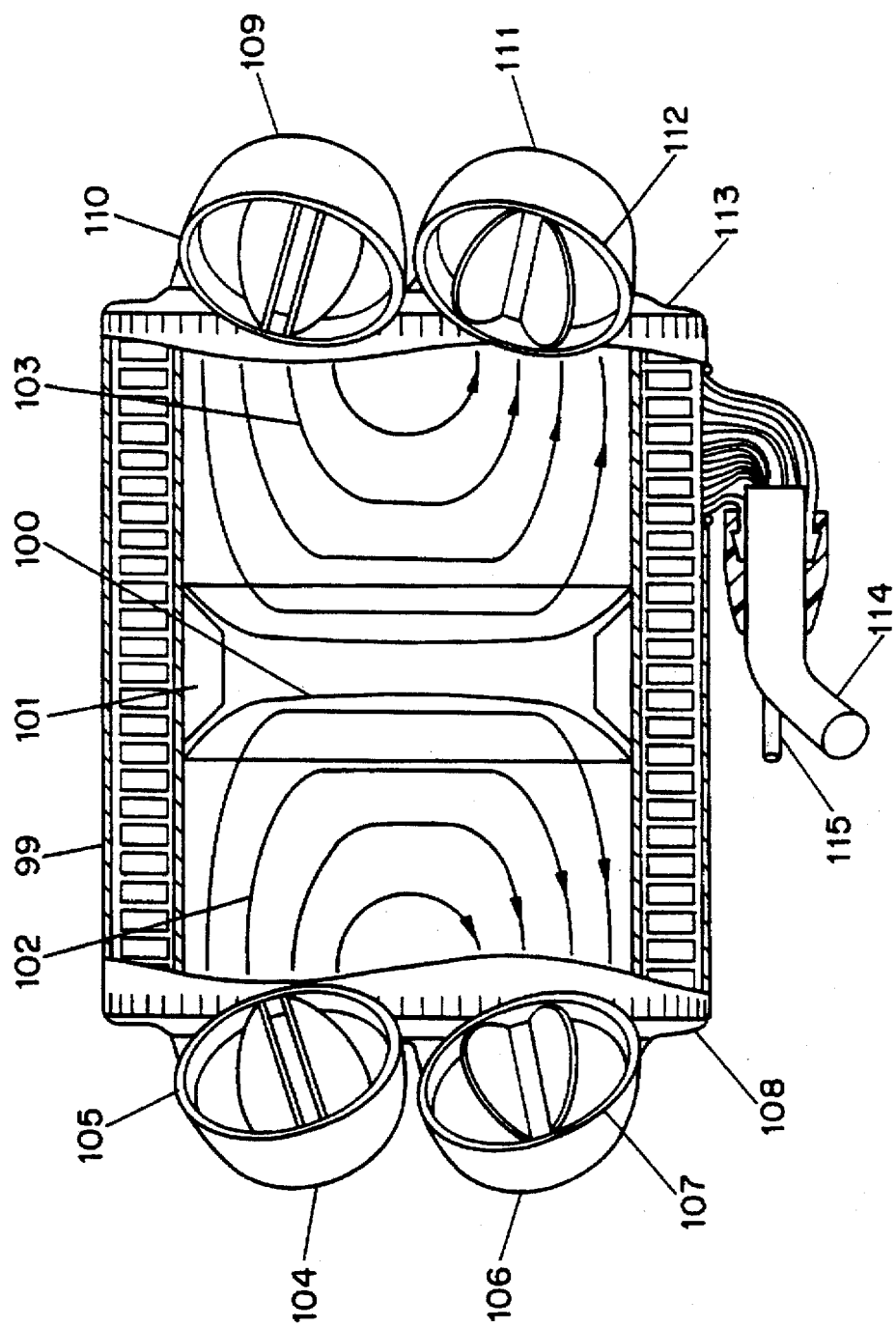
FIG. 17 is a longitudinal sectional view showing a surgically implantable pump arranged in accordance with the invention and configured as a simplex total artificial heart.
Figure 18:
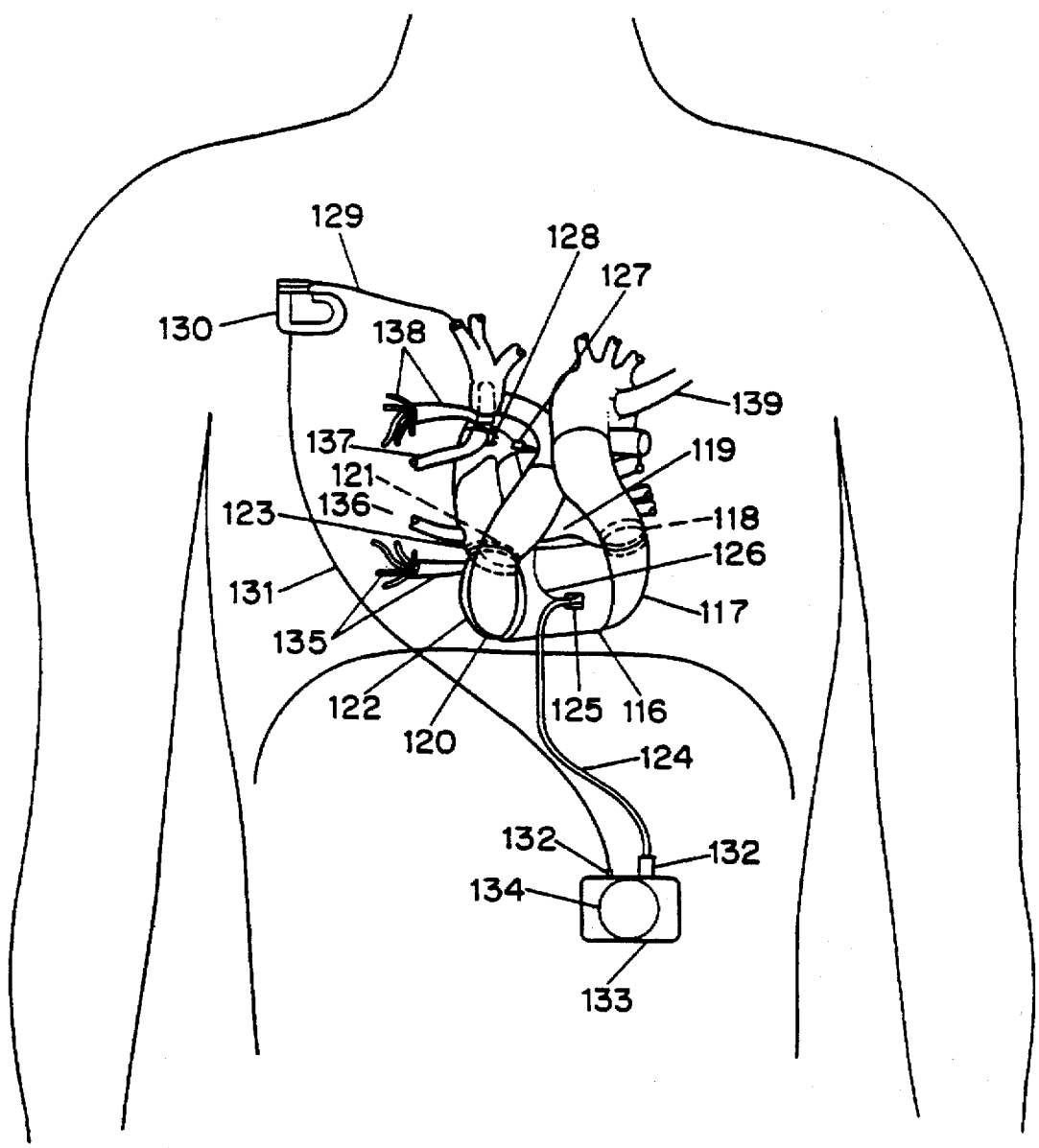
FIG. 18 is a schematic illustration showing the anatomical arrangement of the surgically implantable pump shown in FIG. 17 implanted in a simplex total artificial heart configuration.

FIG. 17 shows a cut-away view of a simplex TAH pump module 99 and FIG. 18 shows the simplex TAH module implanted in a recipient. The pump module 99 is similar to the pump modules previously discussed, except that the piston-valve is replaced by a piston 100 consisting of a solid piece of corrosion-resistant material machined to have concave faces as shown and a circumferential groove in which a magnet and pole piece assembly 101 is mounted. The blood contacting and sliding surfaces of the piston 100 and pump module 99 may be coated with a non-thrombogenic, low friction and wear-resistant material of the type discussed above with respect to other pump modules. The concave faces of the piston promote semicircular flow patterns 102 and 103 which ensure substantially complete exchange of blood during each pumping stroke and washing of the piston faces.

Two conduits 104 and 106 connected to the left end of the module bend upwardly as viewed in the drawing at a sharp angle and contain corresponding check valves 105 and 107 at a location above the level of the pump module, as best seen in FIG. 18. Similarly, two conduits 109 and 111 are bent upwardly from the right end of the pump module and contain corresponding check valves 110 and 112.

In operation, as the piston 100 is driven toward the right as viewed in the drawing, blood is inducted through the conduit 104, which is a conventional synthetic graft or otherwise biocompatible material that may be externally reinforced to prevent collapse. The check valve 105, which may be any conventional prosthetic heart valve, is oriented to permit flow through the conduit 104 only in the direction into the pump module. The conduit 106 is similar in construction to the conduit 104 and both conduits are integrally connected along the centerline of the left side of the pump module to ensure a hemostatic seal. The valve 107 in the conduit 106 is similar to the valve 105 except it is oriented in the opposite direction to prevent flow of blood into the pump module from the conduit 106 as the piston moves to the right. The integrally connected conduits 104 and 106 are hemostatically attached to the pump module by a retaining ring 108, in a manner similar to the retention methods discussed above with respect to other pump modules.

In the conduits 109 and 111 at the opposite end of the pump module, the valve 110 is similar to the valve 105 and is oriented to prevent discharge of blood into the conduit 109 as the piston moves to the right and the valve 112 is similar to the valve 107 and is oriented to permit discharge of blood as the piston moves to the right. The conduits 109 and 111 are attached to the pump module by a retaining ring 113 which is similar to the retaining ring 108. As the piston reverses and moves to the left, the valve 105 shuts to prevent discharge of blood while the valve 107 opens to permit discharge of blood. Likewise, the valve 110 opens to permit inflow of blood while the valve 112 shuts to prevent back filling the pump with blood. A main lead bundle 114 and an epicardial lead 115 can be implemented similarly to previously described pump modules.

FIG. 18 shows an anatomical arrangement of a pump module 116 like the module 99 implanted in the simplex TAH configuration. As in FIG. 15 both of the recipient's ventricles have been removed, leaving only the right and left atria of the native heart. A conduit 117 connects the pump module 116 to the recipient's aorta. A check valve 118 of the type discussed above is located inside the conduit 117 and oriented to permit blood flow toward the aorta only. Another conduit 119 connects the pump module to the recipient's left atrium and incorporates a check valve (not visible) of the type discussed earlier that permits blood flow from the left atrium into the pump module only. A conduit 120 connects the pump module to the recipient's pulmonary artery. A further valve 121 of the type discussed above is oriented to permit blood flow from the pump module toward the pulmonary artery only, and a conduit 122 connects the pump module to the recipient's right atrium. In addition, a check valve 123 in the conduit 120 permits blood flow from the recipient's right atrium to the pump module only as discussed earlier.

A main lead bundle 124 originates at a hermetically sealed penetration 125 in the pump module along with an epicardial lead 126 leading to an epicardial lead electrode 127 which can be placed near a sinus node 128 at the right atrium of the recipient. An endocardial pacemaker ECG lead 129 extends from a pacemaker 130 through the recipient's superior vena cava to the right atrium. The pacemaker can provide an amplified ECG and/or marker channel signal to the controller as in previously described embodiments via a subcutaneous lead bundle 131. This lead bundle and the main lead bundle terminate with hermetically sealed connectors 132 at a controller enclosure 133, which can incorporate charging and telemetry coils 134 as in previously described embodiments.

The simplex TAH arrangement shown in FIG. 18 includes appropriate clamps and cannulae 135, 136, 137, 138, and 139, and is compatible with conventional cardiopulmonary bypass configurations.

A surgically implantable pump in accordance with the invention provides significant advantages over conventional assist devices. For example, it optimizes interaction with the native ventricle so as to recover and utilize as much of the residual ventricular function as possible. By placing the pump in the outflow tract of the ventricle being assisted, and by timing the pumping movement of the piston-valve to occur concurrent with native heart contraction, optimal ventricular assist device interaction is obtained. As the piston-valve moves away from the heart at the initiation of native ventricular ejection, the piston-valve leaflets close and blood in the pump cylinder is propelled into the arterial system. The movement of the piston-valve down the cylinder creates a low pressure, or unloaded, area behind the advancing piston-valve. In the absence of any native ventricular contraction, blood is drawn out of the native ventricle by the negative pressure gradient created by the movement of the piston-valve. When residual ventricular function exists, the impaired, but still contracting, ventricle ejects into the unloaded ventricular outflow tract.

This synchronized, direct unloading of the impaired ventricle has many important advantages. The native ventricle is allowed to contract and empty at least the stroke volume of the surgically implantable blood pump. This prevents the continued dilation of the native ventricle which has many deleterious effects on myocardial blood flow and systolic contractile mechanics. In addition, diastolic coronary filling is improved since the backstroke of the piston-valve during diastole is expected to slightly increase the aortic root pressure above what it would normally be during diastole, much in the way that an intra-aortic balloon pump augments diastolic coronary flow. This occurs due to the slight gradient across the open piston-valve and increases the proximal aortic root pressure, and thus the coronary artery perfusion pressure during backstroke of the piston-valve.

The increase in diastolic coronary artery perfusion pressure, combined with smaller ventricular size, improved myocardial blood flow and decreased demands placed on the native ventricle during systole, result in an optimal reparative environment for an injured ventricle. This reparative "resting" of an injured ventricle allows the myocardium to heal and begin to contribute to meeting the demands of its respective circulation.

Initially, when a surgically implantable pump in accordance with the invention is implanted, a severely injured ventricle will contribute minimally in this regard. After a variable amount of time has passed, however, the injured ventricle will have benefited from the aforementioned reparative conditions and will continue to increase its contribution up to a finite level limited only by its degree of permanent injury. Moreover, as the ventricle recovers and begins to eject with more force, the pressure gradient across the closed advancing piston-valve drops with a resulting decrease in resistance to valve movement and the current drawn by the linear motor. Thus, an increase in native ventricular contribution is not only beneficial to the health of the patient, but in addition, actually serves to decrease pump wear and the need for battery recharging.

Another advantage of a surgically implantable pump in accordance with the invention is that it does not significantly alter the normal blood path through the heart. Conventional devices presently available utilize bulky, thrombosis-promoting cannulas to drain blood from the atrium or the ventricular apex into a peripheral shunt, thereby promoting flow patterns which markedly diverge from normal and therefore promote turbulent eddies, stasis and thrombus formation. In contrast, for a VLAD in accordance with the present invention, the entire blood volume enters the ventricle from the atrium and is subsequently ejected out of the ventricular flow tract by a normal cardiac cycle of full filling during diastole and full emptying during systole. This synchronized interaction with the assisted ventricle helps to minimize eddy formation and stasis and therefore the potential for embolism or thrombus.

Another advantage of a surgically implantable pump in accordance with the invention is a reduced risk of associated right ventricular failure. Distortion of biventricular geometry, by either distention or decompression of the left ventricle results in compromise of normal ventricular interdependence and causes right ventricular failure. Often, this right ventricular failure may be severe enough to require implantation of a right ventricular assist device. As noted above, the pump promotes normal left ventricular filling and emptying. Thus, it promotes the return to and maintenance of normal biventricular geometry and allows normal biventricular interdependence and function. Similar maintenance of normal biventricular interaction is expected when the surgically implantable pump is utilized as an isolated right ventricular assist device.

A further advantage of a surgically implantable pump in accordance with the invention is the maintenance of lower ventricular filling pressures due to filling of the pump in association with the direct unloading of the impaired ventricle. Lower filling pressures are much more physiologic and better tolerated than the higher filling pressures which characterize conventional fill-to-empty devices.

Another advantage provided by the invention is a linear fluid path which avoids unnecessary angulation of blood flow. This is especially important as conventional surgically implantable pumps typically create swirling eddies at the inlet and outlet of the pump thereby resulting in thrombus formation. Swirling, low velocity eddies are essentially eliminated in a surgically implantable pump in accordance with the invention due to the high-flow washing of pump surfaces by blood during ventricular ejection. All blood contacting surfaces of the surgically implantable pump are washed with every heart beat. In addition, the in-line arterial placement of the pump eliminates the long inflow and outflow conduits associated with conventional shunt type ventricular assist devices and allows for a minimum amount of blood-contacting surfaces. In-line arterial placement also allows for enclosure of the pump in the pericardium.

Although the pump described herein may be used in implantable blood pumps, it is also useful as a blood pump which is not surgically implanted inside the body of a patient. In particular, pumps in accordance with the invention might be useful in cardiopulmonary bypass machines, which are used during cardiac surgery but which are not implanted in the patient's body, or in extracorporeal cardiac support devices. The pump module of the invention may also be used as a compact, efficient pump for conveying liquids other than blood.

Although the invention has been described herein with reference to specific embodiments, many modifications and variations therein will readily occur to those skilled in the art. Accordingly, all such variations and modifications are included within the intended scope of the invention.

We claim:

1. A total artificial heart comprising a first surgically implantable pump and a second surgically implantable pump, each pump including a hollow cylinder, a piston slidably positioned in the cylinder for longitudinal movement therein, a permanent magnet member fixedly attached to the piston for movement therewith and having axially spaced magnet poles directed radially outwardly toward the outer surface of the piston, an array of electrical windings spaced axially along the hollow cylinder, and high permeability, high saturation magnetic material between the spaced electrical windings, whereby the flux produced by the permanent magnet poles links the electrical windings, the inlet end of the first pump being connectable to a right atrium, the outlet end of the first pump being connectable to a pulmonary artery, the inlet end of the second pump being connectable to a left atrium, and the outlet end of the second pump being connectable to an aorta, and control means for sequentially energizing the electrical windings in the array in each pump in a controlled manner so as to exert an axial force on the piston in each pump causing the corresponding piston to move longitudinally through the hollow cylinder in a controlled manner in synchrony with the sequential energization of the electrical windings.

2. A total artificial heart in accordance with claim 1 wherein each pump further comprises an inflected conduit at the outlet end, and the inflected conduit at the outlet end of the first pump redirects and carries blood upwardly, to the pulmonary artery and the inflected conduit at the outlet end of the second pump redirects and carries blood upwardly to the ascending aorta.

3. A total artificial heart in accordance with claim 1 wherein each pump further comprises an inflected conduit at the inlet end and the inflected conduit at the inlet end of the first pump redirects and carries blood entering from the right atrium into the first pump inlet and the inflected conduit at the inlet end of the second pump redirects and carries blood entering from the right atriuminto the second pump inlet.

4. A total artificial heart in accordance with claim 1 further comprising one-way valves located at the outlet end of each pump wherein the one-way valves permit blood flow toward the pulmonary artery and ascending aorta and prevent blood flow toward the outlet of each pump.

5. A total artificial heart in accordance with claim 1 further comprising one-way valves located at the inlet end of each pump wherein the one-way valves permit blood flow toward each pump inlet end and prevent blood flow toward the atria.

6. A total artificial heart in accordance with claim 1 further comprising a pacemaker connected to the control means wherein the control means synchronizes the movement of the piston in each pump in response to signals provided from the pacemaker.

7. A total artificial heart in accordance with claim 1 wherein the control means includes a common lead bundle and wherein the common lead bundle includes branches which provide equivalent control signals to the array of electrical windings in each pump.

8. A total artificial heart in accordance with claim 1 including epicardial leads leading from a patient's native heart to the control means and wherein the control means synchronizes the reciprocation of the piston in response to electrocardiogram signals from the epicardial leads.

9. A method for maintaining blood flow in a patient comprising the steps of providing a total artificial heart comprising a first surgically implantable pump and a second surgically implantable pump, each pump including a hollow cylinder, a piston slidably positioned in the cylinder for longitudinal movement therein, a permanent magnet member fixedly attached to the piston for movement therewith and having axially spaced magnet poles directed radially outwardly toward the outer surface of the piston, an array of electrical windings spaced axially along the hollow cylinder, and high permeability, high saturation magnetic material between the spaced electrical windings, whereby the flux produced by the permanent magnet poles links the electrical windings, the inlet end of the first pump being connectable to a right atrium, the outlet end of the first pump being connectable to a pulmonary artery, the inlet end of the second pump being connectable to a left atrium, and the outlet end of the second pump being connectable to an aorta, and control means for sequentially energizing the electrical windings in the array in each pump in a controlled manner so as to exert an axial force on the piston in each pump causing the corresponding piston to move longitudinally through the hollow cylinder and blood to flow into and through each pump, the piston moving in a controlled manner in synchrony with the sequential energization of the electrical windings, connecting the inlet end of the first pump to a patient's right atrium and the outlet end of the first pump to a patient's pulmonary artery and connecting the inlet end of the second pump to a patient's left atrium and the outlet end of the second pump to a patient's aorta.

10. A method for maintaining blood flow in a patient in accordance with claim 9 comprising providing an inflected conduit at the outlet end of each pump, redirecting and carrying blood through the inflected conduit at the outlet end of the first pump blood upwardly to the pulmonary artery and redirecting and carrying blood through the inflected conduit at the outlet end of the second pump upwardly to the ascending aorta.

11. A method for maintaining blood flow in a patient in accordance with claim 9 comprising providing one-way valves at the outlet end of each pump, permitting blood flow through the one-way valves toward the pulmonary artery and ascending aorta and preventing blood flow through the one-way valves toward the outlet end of each pump.

12. A method for maintaining blood flow in a patient in accordance with claim 9 comprising providing one-way valves at the inlet end of each pump, permitting blood flow thought the one-way valves toward each pump inlet end and preventing blood flow through the one-way valves toward the atria.

13. A method for maintaining blood flow in a patient in accordance with claim 9 comprising providing a pacemaker connected to the control means and synchronizing the movement of the piston with the control means in each pump in response to signals provided from the pacemaker.

14. A method for maintaining blood flow in a patient in accordance with claim 9 wherein the control means includes a common lead bundle having branches and sending equivalent control signals from the branches to the array of electrical windings in each pump.

15. A method for maintaining blood flow in a patient in accordance with claim 9 comprising providing epicardial leads, connecting the epicardial leads to a parent's native heart and to the control means and synchronizing the reciprocation of the piston with the control means in response to electrocardiogram signals from the epicardial leads.

* * * * *

UNITED STATES PATENT AND TRADEMARK OFFICE
CERTIFICATE OF CORRECTION

PATENT NO. : 5,693,091

DATED : December 2, 1997

INVENTOR(S) : Carl O. Larson, Jr. et al.

It is certified that error appears in the above-indentified patent and that said Letters Patent is hereby corrected as shown below:

On the title page, item [56]:

Page 3, 1st col., third-from-bottom line, "Antomic" should read --Anatomic--;

Col. 1, line 11, add --Both U.S. Serial Nos. 08/035,788 and 07/926,779 are incorporated by reference herein.--;

Col. 6, line 9, "tint" should read --first--;

Col. 6, line 9, "fight" should read --right--;

Col. 6, line 15, "a oxen" should --exert--;

Col. 7, line 30, "ration;" should read --ration.--;

Col. 23, line 65, "all together" should read --altogether--;

Col. 32, line 51, "pump blood" should read --pump--;

UNITED STATES PATENT AND TRADEMARK OFFICE
CERTIFICATE OF CORRECTION

PATENT NO. : 5,693,091
DATED : December 2, 1997
INVENTOR(S) : Carl O. Larson, et al.

It is certified that error appears in the above-indentified patent and that said Letters Patent is hereby corrected as shown below:

Col. 34, line 5, "parent's" should read --patient's--.

Signed and Sealed this

Fourteenth Day of July, 1998

Attest:

BRUCE LEHMAN

*Attesting Officer*              *Commissioner of Patents and Trademarks*